(12) United States Patent
Sakata et al.

(10) Patent No.: US 9,661,993 B2
(45) Date of Patent: May 30, 2017

(54) ENDOSCOPE

(71) Applicant: OLYMPUS CORPORATION, Tokyo (JP)

(72) Inventors: Hajime Sakata, Tokyo (JP); Naoya Shimada, Iruma (JP)

(73) Assignee: OLYMPUS CORPORATION, Tokyo (JP)

(*) Notice: Subject to any disclaimer, the term of this patent is extended or adjusted under 35 U.S.C. 154(b) by 144 days.

(21) Appl. No.: 14/629,637

(22) Filed: Feb. 24, 2015

(65) Prior Publication Data
US 2015/0164304 A1 Jun. 18, 2015

Related U.S. Application Data

(63) Continuation of application No. PCT/JP2014/058422, filed on Mar. 26, 2014.

(30) Foreign Application Priority Data

Mar. 28, 2013 (JP) ................. 2013-070058

(51) Int. Cl.
A61B 1/00 (2006.01)
A61B 1/005 (2006.01)
G02B 23/24 (2006.01)
A61B 1/04 (2006.01)
A61B 1/012 (2006.01)

(52) U.S. Cl.
CPC .......... *A61B 1/0055* (2013.01); *A61B 1/0008* (2013.01); *A61B 1/0011* (2013.01); *G02B 23/2476* (2013.01); *A61B 1/0125* (2013.01)

(58) Field of Classification Search
CPC ... A61B 1/0055; A61B 1/0011; A61B 1/0008; A61B 1/0125; A61B 1/00135; A61B 1/042; G02B 23/2476
See application file for complete search history.

(56) References Cited

U.S. PATENT DOCUMENTS 5,591,120 A    1/1997   Machida et al.

FOREIGN PATENT DOCUMENTS

| JP | 04-371129 A | 12/1992 |
| JP | 08-152564 A | 6/1996 |
| JP | 08-308791 A | 11/1996 |

(Continued)

OTHER PUBLICATIONS

International Search Report dated Jun. 24, 2014 issued in PCT/JP2014/058422.

(Continued)

*Primary Examiner* — Timothy J Neal
(74) *Attorney, Agent, or Firm* — Scully, Scott, Murphy & Presser, P.C.

(57) ABSTRACT

An endoscope includes an insertion portion, a flexible member, a connecting member the proximal end side portion of which is fixed to the distal end side of the flexible member, an outer sheath, a first filling agent that is applied on the outer circumference side of the flexible member in such a manner as to come into contact with at least the distal end side of the outer sheath, an annular member that covers at least the outer circumference of the first filling agent, a protruding portion, and a second filling agent that is applied so as to continuously cover at least the outer circumference of the annular member and the outer circumference on the distal end side of the outer sheath.

16 Claims, 19 Drawing Sheets

(56) References Cited

FOREIGN PATENT DOCUMENTS

| JP | 11-225947 A | 8/1999 |
| JP | 2000-041937 A | 2/2000 |
| JP | 2006-212278 A | 8/2006 |
| JP | 2009-291434 A | 12/2009 |
| JP | 2012-095719 A | 5/2012 |

OTHER PUBLICATIONS

Japanese Office Action dated Sep. 16, 2014 issued in JP 2014-536805.
Extended Supplementary European Search Report dated Mar. 7, 2016 from related European Application No. 14 77 2766.3.

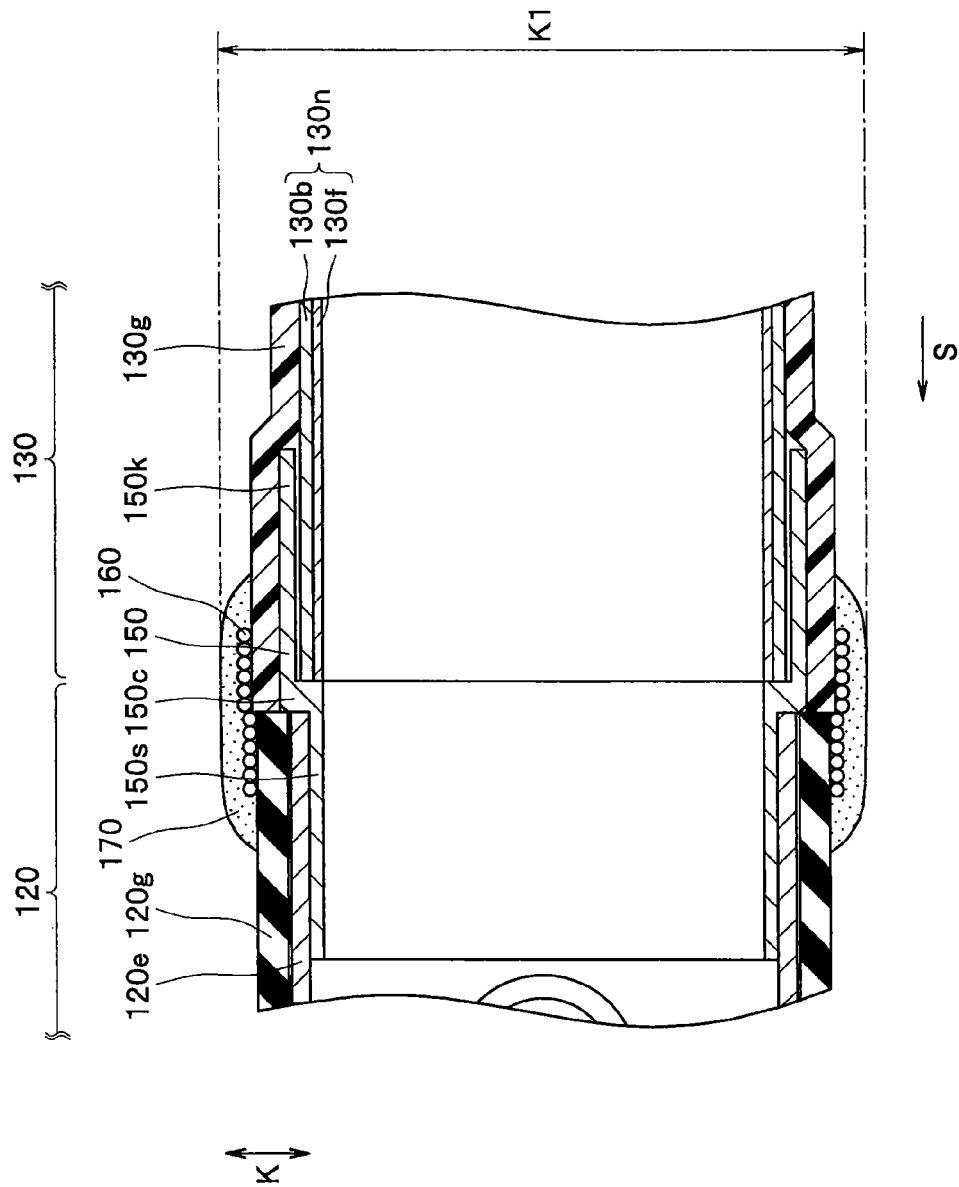

ENDOSCOPE

CROSS REFERENCE TO RELATED APPLICATION

This application is a continuation application of PCT/JP2014/058422 filed on Mar. 26, 2014 and claims benefit of Japanese Application No. 2013-070058 filed in Japan on Mar. 28, 2013, the entire contents of which are incorporated herein by this reference.

BACKGROUND OF INVENTION

1. Field of the Invention

The present invention relates to an endoscope in which a first cylindrical member configuring an elongated insertion portion to be inserted into a subject and a second cylindrical member are coupled by a connecting member.

2. Description of the Related Art

In recent years, endoscopes have come into widespread use in a medical field and an industrial field. With an endoscope used in the medical field, an elongated insertion portion is inserted into a body cavity of a subject to observe an organ in the body cavity, or to perform various treatments using a treatment instrument that is inserted into a channel included in the endoscope as necessary.

In addition, with an endoscope used in the industrial field, an elongated insertion portion of the endoscope is inserted into an object such as a jet engine and piping in a factory to perform inspection such as observation of a flaw, a corrosion, and the like of a portion to be examined in the object and various measures.

The insertion portion of the endoscope has a well-known configuration including a distal end portion that is positioned at a distal end of the insertion portion in an inserting direction (hereafter, simply referred to as a distal end) and that is provided therein with an image pickup unit for picking up an image of a subject, a bending portion that is provided being connected to a proximal end in the inserting direction of the distal end portion (hereafter, simply referred to as a proximal end) and that is bendable in a plurality of directions, and a flexible tube portion that is elongated and has flexibility and that is provided being connected to the proximal end of the bending portion.

Here, a well-known configuration includes a connecting member used for connecting the proximal end of the bending portion and the distal end of the flexible tube portion.

FIG. 19 is a partial cross sectional view showing a conventional connection configuration between the proximal end of a bending portion and the distal end of a flexible tube portion. Japanese Patent Application Laid-Open Publication No. 2012-95719 discloses, as shown in FIG. 19, a configuration in which the proximal end of a bending portion 120 and the distal end of a flexible tube portion 130 are connected using a connecting member 150 that is folded into a crank-shape at a halfway position in an inserting direction S (hereafter, simply referred to as a halfway position).

More specifically, as shown in FIG. 19, the connecting member 150 is formed into a cylindrical shape, and includes a crank portion 150$c$ formed at the halfway position. In the connecting member 150, this causes a distal end side portion 150$s$ that is positioned closer to a distal end side in the inserting direction S (hereafter, simply referred to as a distal end side) than the crank portion 150$c$, to be positioned inside the insertion portion in a radial direction K as compared with a proximal end side portion 150$k$ that is positioned closer to a proximal end side in the inserting direction (hereafter, simply referred to as a proximal end side) than the crank portion 150$c$.

In addition, the bending portion 120 is configured on the outer circumference of the distal end side portion 150$s$ of the connecting member 150, and the outer circumference of the distal end side portion 150$s$ is covered with a bending cover 120$g$ being a second covering member. In addition, a bending piece 120$e$ is fixed that is positioned at the most rearward (hereafter, referred to as rearward) position in the inserting direction S out of a plurality of bending pieces 120$k$ being second cylindrical members that are covered with the bending cover 120$g$. Note that the respective proximal ends of the bending piece 120$e$ and the bending cover 120$g$ are caused to abut the distal end of the crank portion 150$c$ of the connecting member 150.

Furthermore, on the inner circumference of the proximal end side portion 150$k$ of the connecting member 150, a distal end side of a braid 130$b$ is fixed to an inner circumferential portion being a first cylindrical member that configures the flexible tube portion 130 and a flex 130$f$ having a cylindrical shape is fixed to the braid 130$b$ (hereafter, the braid 130$b$ whose inner circumference is fixed to the flex 130$f$ will be referred to as a flexible member 130$n$). Note that the distal end of the flexible member 130$n$ is caused to abut the proximal end of the crank portion 150$c$ of the connecting member 150.

In addition, the distal end side of an outer sheath 130$g$ being a first covering member that covers the outer circumference of the braid 130$b$ is fixed on the outer circumference of the proximal end side portion 150$k$ of the connecting member 150, being caused to abut the proximal end of the bending cover 120$g$.

In addition, although not shown in Japanese Patent Application Laid-Open Publication No. 2012-95719, in order to secure water-tightness of the connecting portion between the proximal end of the bending portion 120 and the distal end of the flexible tube portion 130 after coupling the bending portion 120 and the flexible tube portion 130 using the connecting member 150, as shown in FIG. 19, a binding thread 160 is normally wound on the outer circumference on the proximal end side of the bending cover 120$g$ and on the outer circumference on the distal end side of the outer sheath 130$g$. Furthermore, an adhesive 170 is applied so as to cover the binding thread 160, and a gap between the proximal end of the bending portion 120 and the distal end of the flexible tube portion 130. That is, configurations subjected to so-called thread winding and bonding are well-known.

In addition, the distal end side of the outer sheath 130$g$ is fixed on the outer circumference of the braid 130$b$ in such a manner that the distal end of the outer sheath 130$g$ abuts the proximal end of the proximal end side portion 150$k$ of the connecting member 150. In addition, conceivable configurations include one in which the reduction of the outer diameter of the above-described fixed portion is achieved by performing the thread winding and bonding not only on the outer circumference on the proximal end side of the bending cover 120$g$, but also on the outer circumference of the proximal end side portion 150$k$ of the connecting member 150 and on the outer circumference on the distal end side of the outer sheath 130$g$.

Furthermore, conceivable configurations include one in which the reduction is achieved and the connecting operation is simplified by securing water-tightness of the above-described connecting portion with only the adhesive 170, without using the binding thread 160.

SUMMARY OF THE INVENTION

An endo scope according to one aspect of the present invention includes an elongated insertion portion that is inserted into a subject; a first cylindrical member that configures the insertion portion and extends along an inserting direction of the insertion portion; a connecting member a proximal end side of which in the inserting direction is fixed to a distal end side of the first cylindrical member in the inserting direction; a first covering member that is caused to cover an outer circumference of the first cylindrical member, and at least a distal end side of which in the inserting direction is positioned, in the radial direction, outside an outer circumference on the proximal end side of the connecting member; a first filling agent that is applied on an outer circumference side of the first cylindrical member in a radial direction of the insertion portion, in such a manner as to come into contact with at least the distal end side of the first covering member; an annular member that covers at least an outer circumference of the first filling agent; a protruding portion that is formed on a distal end side of the annular member in the inserting direction, the protruding portion being folded inward in the radial direction in such a manner as to abut an outer circumference of the connecting member, and being positioned on the distal end side in the inserting direction with respect to the distal end of the first covering member in the inserting direction; and a second filling agent that is applied so as to continuously cover at least an outer circumference of the annular member and an outer circumference on the distal end side of the first covering member along the inserting direction.

An endoscope according to another aspect of the present invention includes an elongated insertion portion that is to be inserted into a subject; a first cylindrical member that configures the insertion portion and extends along an inserting direction of the insertion portion; a connecting member a proximal end side of which in the inserting direction is fixed to a distal end side of the first cylindrical member in the inserting direction, and that includes an outward flange formed on an outer circumference of the connecting member, a distal end of the first cylindrical member in the inserting direction being caused to abut the outward flange; a first covering member that is caused to cover an outer circumference of the first cylindrical member; a first filling agent that is applied on an outer circumference side of the first cylindrical member in a radial direction of the insertion portion, in such a manner as to come into contact with at least a distal end side of the first covering member in the inserting direction; an annular member that covers at least an outer circumference of the first filling agent; and a second filling agent that is applied so as to continuously cover at least an outer circumference of the annular member and an outer circumference on the distal end side of the first covering member along the inserting direction.

BRIEF DESCRIPTION OF THE DRAWINGS

FIG. 19 a partial cross sectional view showing a conventional connection configuration between the proximal end of the bending portion and the distal end of the flexible tube portion.

DETAILED DESCRIPTION OF THE PREFERRED EMBODIMENT(S)

Embodiments of the present invention will be described below with reference to the drawings.

(First Embodiment)

Figure 1:
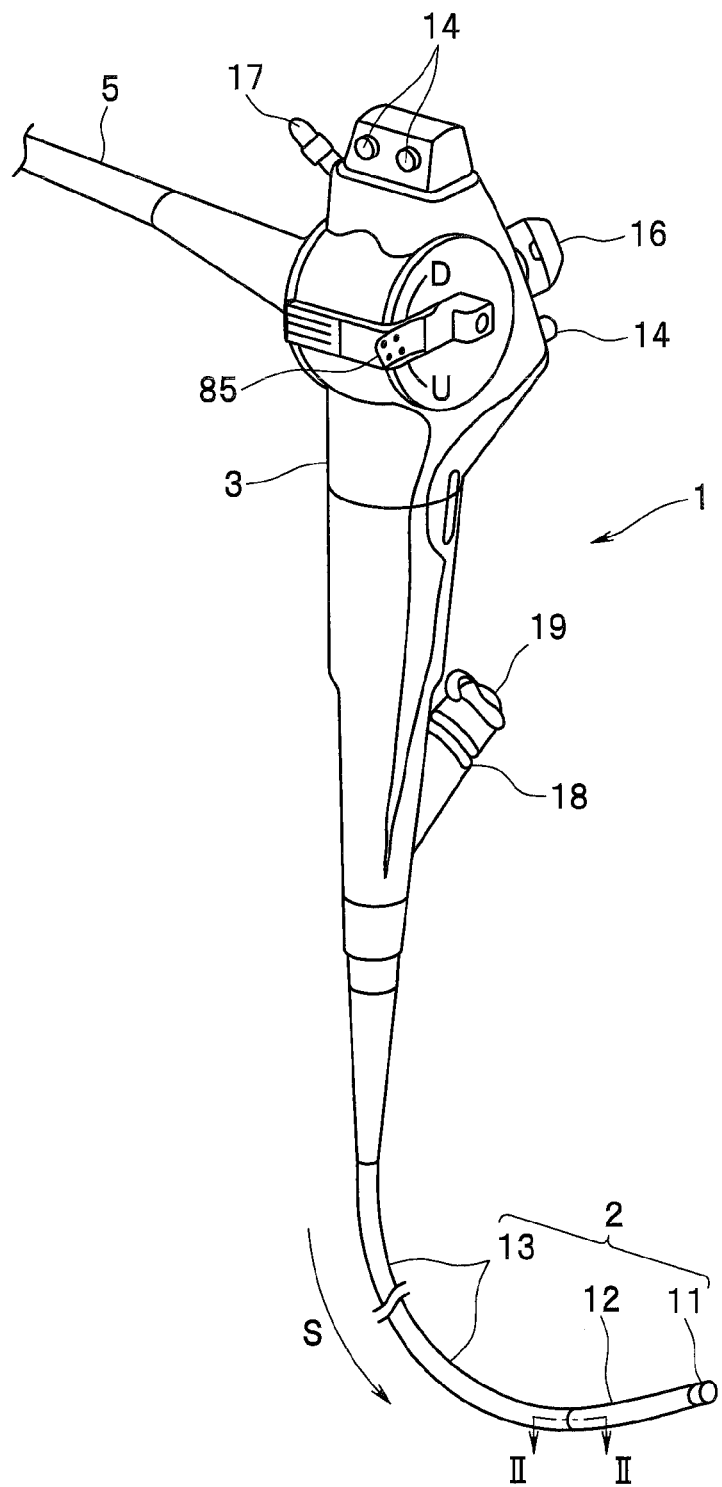
FIG. 1 is a partial perspective view showing an endoscope of a first embodiment of the present invention.
Figure 2:
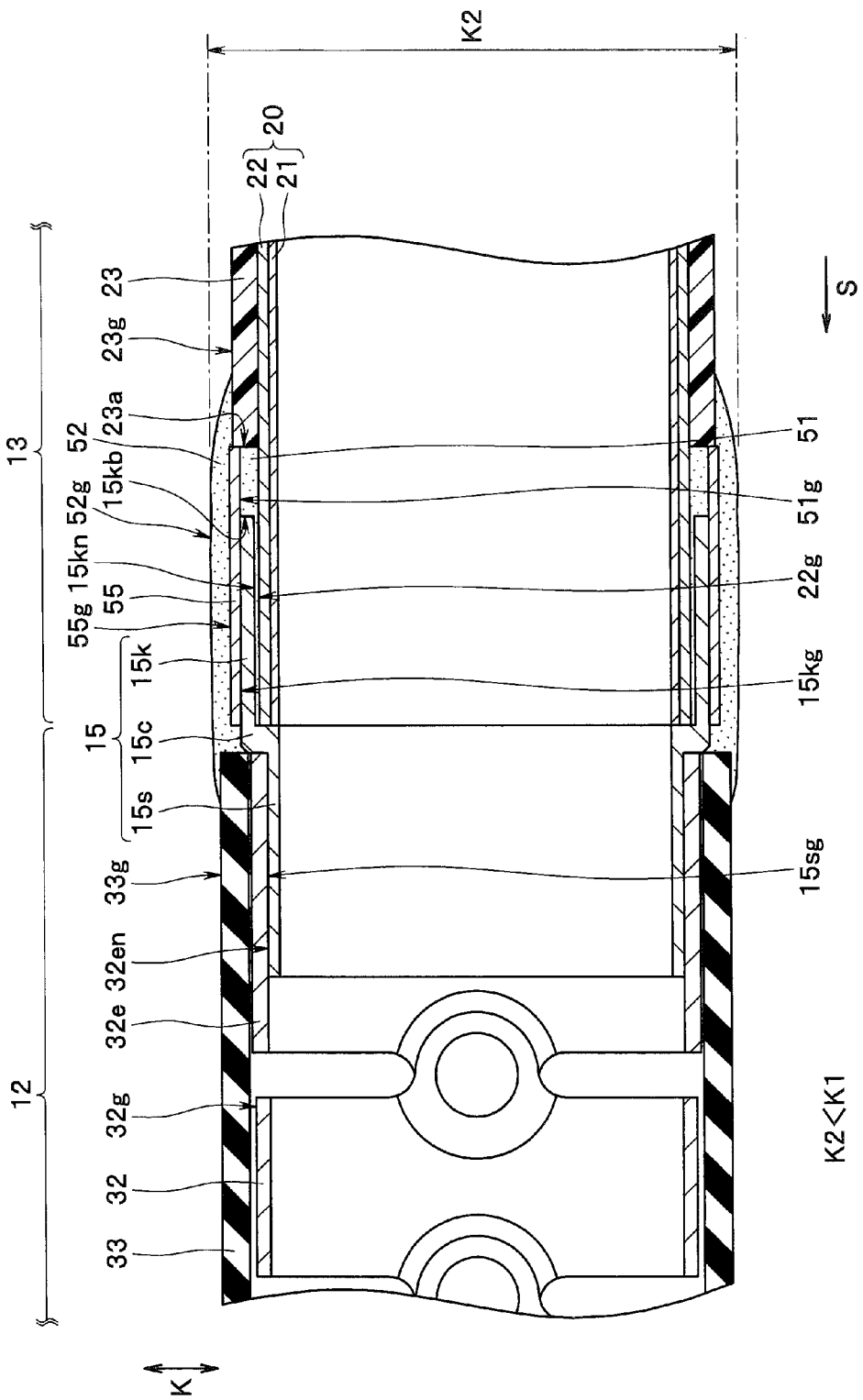
FIG. 2 is a partial cross sectional view showing a connecting portion between the proximal end of a bending portion and the distal end of a flexible tube portion taken along a line II-II in FIG. 1, under magnification.

FIG. 1 is a partial perspective view showing an endoscope of this first embodiment, and FIG. 2 is a partial cross sectional view showing a connecting portion between the proximal end of a bending portion and the distal end of a flexible tube portion taken along a line II-II in FIG. 1 under magnification.

As shown in FIG. 1, an endoscope 1 includes an insertion portion 2 that is inserted into a subject, being elongated along an inserting direction S, and an operating portion 3 that is provided being connected to the proximal end of the insertion portion 2. In addition, the endoscope 1 includes a universal cord 5 extended from the operating portion 3, and a connector, which is not shown, provided to the extension end of the universal cord. In addition, the connector of the endoscope 1 is freely connected to an image processing device and a light source apparatus, and the like, which are not shown, such that the endoscope 1 is freely connected to an external device of the endoscope 1.

The insertion portion 2 includes a rigid distal end portion 11 and a bending portion 12 that is provided being connected to the proximal end of distal end portion 11, and a flexible tube portion 13 provided being connected to the proximal end of the bending portion 12, which configure the main part of the insertion portion 2, in an order from the distal end side. The distal end portion 11 is provided therein with an image pickup unit and the like, which are not shown. The bending portion 12 is freely bent in a plurality of directions, for example, two vertical directions. The flexible tube portion 13 has flexibility and is formed to be flexible.

Note that a plurality of bending pieces 32 (refer to FIG. 2) being second cylindrical members configuring the insertion portion 2 are connected in the inserting direction S, which allows the bending portion 12 to be freely bent, for example, in vertical two directions.

In addition, the bending directions of the bending portion 12 are not limited to the vertical two directions, and may be horizontal two directions. Furthermore, the bending direction of the bending portion 12 may be vertical and horizontal four directions, and even further, may be more than four directions.

In addition, as shown in FIG. 2, outer circumferences 32g of the plurality of bending pieces 32 are covered with bending covers 33 being second covering members that protect the bending pieces 32. That is, the bending portion 12 is configured by covering the outer circumferences 32g of the plurality of bending pieces 32 with the bending covers 33.

In addition, the flexible tube portion 13 includes, as shown in FIG. 2, a flexible flex 21 that extends along the inserting direction S and to which a braid 22 made of a mesh tube is fixed. Note that the flex 21 is fixed on the inner circumference of the braid 22. Note that the flex 21 to which the braid 22 is fixed will be referred to below as a flexible member 20.

Note that the flexible member 20 configures a first cylindrical member that configures the insertion portion 2 in the present embodiment.

In addition, as shown in FIG. 2, an outer circumference 22g of the braid 22 is covered with an outer sheath 23 being a first covering member. That is, the flexible tube portion 13 is configured by covering the outer circumference of the flexible member 20, that is, the outer circumference 22g of the braid 22 with the outer sheath 23.

The operating portion 3 is provided with a remote switch 14 for providing an image control instruction such as freeze and release, and a bending operation lever 85 for operating the bending portion 12 to bend. Furthermore, the operating portion 3 is provided with a suction button 16 for performing sucking operation, and a suction pipe sleeve 17 that is provided being communicated to a suction channel, which is not shown, provided in the insertion portion 2. Note that a member to operate the bending portion 12 to bend is not limited to a lever, and may be a pivotable knob or the like.

Furthermore, the operating portion 3 is provided with, on a portion close to the insertion portion 2, a treatment instrument insertion opening 18 to insert treatment instruments such as forceps. The treatment instrument insertion opening 18 is provided detachably with a forceps plug 19.

Next, the configuration of the connecting portion for connecting the proximal end of the bending portion 12 and the distal end of the flexible tube portion 13 will be described with reference to FIG. 2.

As shown in FIG. 2, among the plurality of bending pieces 32 configuring the bending portion 12, the bending piece 32e positioned at the most rearward position is connected to the flexible member 20 configuring of the flexible tube portion 13 by a connecting member 15. This makes the proximal end of the bending portion 12 and the distal end of the flexible tube portion 13 coupled and connected to each other along the inserting direction S.

More specifically, the connecting member 15 is formed into a cylindrical shape, and is folded into a crank-shape at a halfway position in the inserting direction S, that is, has a crank portion 15c at the halfway position. This causes a distal end side portion 15s positioned closer to the distal end side than the crank portion 15c to be positioned, in a radial direction K of the insertion portion 2, inside the proximal end side portion 15k positioned closer to the proximal end side than the crank portion 15c.

In addition, to an outer circumference 15sg of the distal end side portion 15s of the connecting member 15, an inner circumference 32en of the bending piece 32e positioned at the most rearward position in the inserting direction S among the plurality of bending pieces 32 is adhered and fixed. Note that the respective proximal ends of the bending piece 32e and the bending cover 33 are caused to abut to the distal ends of the crank portion 15c.

Note that the purpose of positioning the distal end side portion 15s inside the proximal end side portion 15k in the radial direction K in the connecting member 15 is to prevent the bending piece 32e fixed on the outer circumference 15sg of the distal end side portion 15s and the bending cover 33 with which the outer circumference of the bending piece 32e is covered from largely protruding outward from the proximal end side portion 15k and the outer sheath 23 in the radial direction K. That is, the purpose is to prevent an outer diameter K2 of the above-described connecting portion from increasing.

Furthermore, to an inner circumference 15kn of the proximal end side portion 15k of the connecting member 15, the outer circumference on the distal end side of the flexible member 20, that is, the outer circumference 22g on the distal end side of the braid 22 is adhered and fixed. Note that the distal ends of the flex 21 and the braid 22 are caused to abut the proximal end of the crank portion 15c of the connecting member 15.

This makes the bending piece 32e and the flexible member 20 coupled by the connecting member 15.

In addition, to the inner circumference 15kn of the proximal end side portion 15k of the connecting member 15, in a state the outer circumference 22g on the distal end side of the braid 22 is fixed, a distal end 23a of the outer sheath 23 with which the outer circumference 22g of the braid 22 is covered is positioned at a more rear position from the proximal end 15kb of the proximal end side portion 15k, with an interval. Provision of a separating gap in such a manner secures water-tightness due to the first filling agent 51 to be described hereafter as well as increases the amount of first filling agent 51 without increasing the diameter, which enables more secure fixing of an annular member 55 to be described hereafter.

That is, the outer sheath 23 does not cover the outer circumference 22g of the braid 22 on the distal end side of the braid that is fixed on the inner circumference 15kn of the proximal end side portion 15k, but the outer circumference 22g from a position separated rearward by a predetermined distance from the distal end of the braid 22 to the proximal end of the braid 22, along the inserting direction S. Note that the method of covering the outer sheath 23 is, for example, covering with a heat shrinkable tube or thermal welding with resin.

Furthermore, the first filling agent 51 is applied to the outer circumference 22g of the braid 22 between the distal end 23a of the of the outer sheath 23 and the proximal end 15kb of the proximal end side portion 15k so as to fill a space formed between the distal end 23a and the proximal end 15kb along the inserting direction.

The first filling agent 51 has a function of fixing the annular member 55 to be described hereafter to the outer circumference 15kg of the proximal end side portion 15k of the connecting member 15, as well as a function of securing water-tightness between the proximal end side portion 15k and the flexible tube portion 13.

Figure 6:
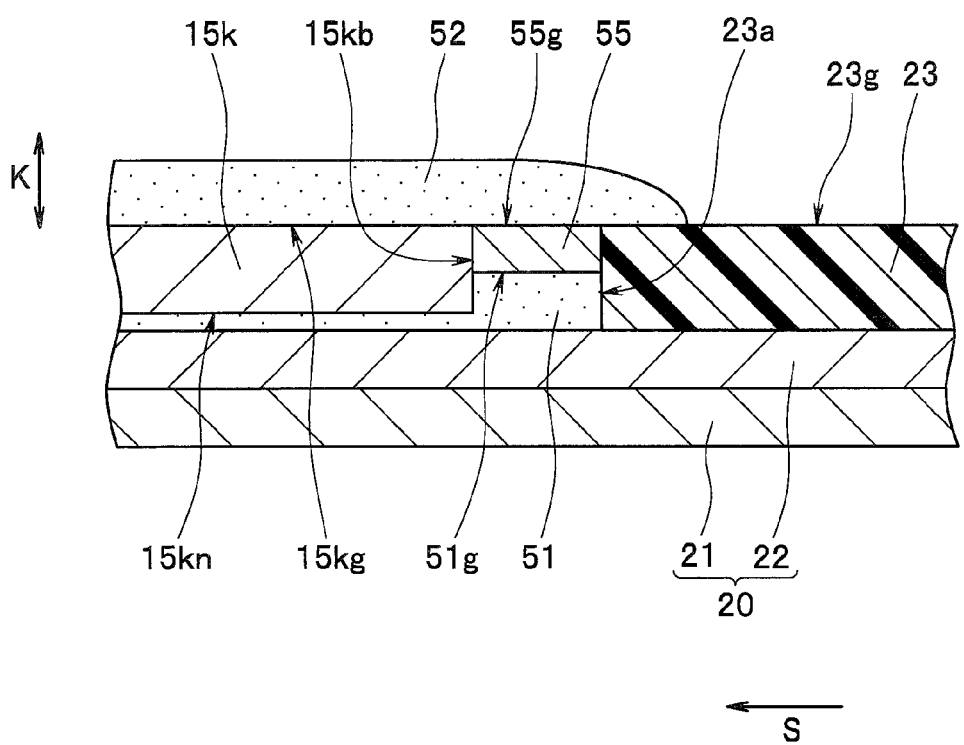
FIG. 6 is a partial cross sectional view showing a modification of the first embodiment, and showing a state that the outer circumference of the first filling agent in FIG. 2 is positioned, in a radial direction, inside the outer circumference of the proximal end side portion of the connecting member, and the annular member covers only the outer circumference of the first filling agent.

Note that the first filling agent 51 is applied such that the outer circumference 51g thereof has the same outer diameter as the outer circumference 15kg of the proximal end side portion 15k, or such that the outer circumference 51g is positioned inside the outer circumference 15kg in the radial direction K as shown in FIG. 6 to be described hereafter.

In addition, the first filling agent 51 is configured by, for example, an adhesive. In addition, the first filling agent 51 may be configured by the same material as second filling agent 52 to be described hereafter, but is preferably configured by a material that has hardness after curing lower than the second filling agent 52, for example, a silicon-based material, which is soft.

This is because the braid 22 having the outer circumference 22g to which the first filling agent 51 is applied is easily deformed due to having flexibility together with the flex 21. For this reason, if the first filling agent 51 after curing is configured by a rigid material, a crack or the like is prone to occur in the first filling agent 51 with the deformation of the braid 22. Conversely, if the first filling agent 51 after curing is configured by a soft material, the first filling agent 51 is easy to be deformed together with the braid 22 when the braid 22 is deformed, which makes a crack or the like difficult to occur in the first filling agent 51.

In addition, the outer circumference 51g of the first filling agent 51 is covered with the annular member 55 the proximal end of which is caused to abut the distal end 23a of the outer sheath 23. The annular member 55 is formed of, for example, a resin or a metal and into a cylindrical shape, and is formed to have such a length that at least the outer circumference 51g of the first filling agent 51 is covered in the inserting direction S. Note that, in FIG. 2, the annular member 55 also covers the outer circumference 15kg of the proximal end side portion 15k of the connecting member 15.

Furthermore, the annular member 55 is formed so as to have a thickness in the radial direction K smaller than the outer sheath 23. This is because the outer diameter K2 of the above-described connecting portion is increased if the annular member 55 is formed to have a large thickness.

In addition, the second filling agent 52 is applied to the outer circumference 55g of the annular member 55 and the outer circumference 23g on the distal end side of the outer sheath 23, such that the outer circumference 55g and the distal end side of the outer circumference 23g are continuously covered along the inserting direction S.

Note that the second filling agent 52 is configured by, for example, an adhesive. In addition, the second filling agent 52 is preferably configured by a material more rigid than the first filling agent 51. This is because the second filling agent 52 is positioned in an outer-most layer in the above-described connecting portion, and thus when the insertion portion 2 is inserted into a conduit or the like, the second filling agent 52 is a member prone to be in contact with the inner wall of the conduit or the like. Therefore, the second filling agent 52 after curing is scraped off on contact if the second filling agent 52 is configured by a soft material. Conversely, if the second filling agent 52 is configured by a rigid material, the second filling agent 52 after curing is difficult to be scraped off even on contact.

In addition, the second filling agent 52 is applied, as shown in FIG. 2, so as to further continuously cover the outer circumference 33g on proximal end side of the bending cover 33 together with the outer circumference 55g of the annular member 55.

The second filling agent 52 is for securing the water-tightness of the proximal end of the bending portion 12 and the water-tightness of the distal end of the flexible tube portion 13, for the connecting member 15. More specifically, the second filling agent 52 is for securing water-tightness between the outer circumference 15sg of the distal end side portion 15s of the connecting member 15 and the inner circumference 32en of the bending piece 32e, between the proximal end of the annular member 55 and the distal end 23a of the outer sheath 23, and between the outer circumference 15kg of the proximal end side portion 15k of the connecting member 15 and the annular member 55.

Here, as described above, the annular member 55 covers the outer circumference 51g of the first filling agent 51, and the proximal end thereof is caused to abut the distal end 23a of the outer sheath 23. This makes the annular member 55 a member for preventing, when an external force is applied to the second filling agent 52 at a distal-end-vicinity position in the flexible tube portion 13 and a crack or the like occurs in the second filling agent 52 at the distal-end-vicinity position of the flexible tube portion 13, the crack from penetrating the first filling agent 51. That is, the annular member 55 is positioned being sandwiched between the first filling agent 51 and the second filling agent 52 in the radial direction K.

Note that the reason that the crack or the like is easy to occur in the second filling agent 52 at the distal-end-vicinity position of the flexible tube portion 13, is that, as described above, the flexible tube portion 13 has a flexibility and is easy to be deformed. That is, this is because the crack or the like is easy to occur in the second filling agent 52 at a position at which the second filling agent 52 is applied to the outer circumference 23g on the distal end side of the outer sheath 23 and the outer circumference 55g of the proximal end side of the annular member 55, with the deformation of the flexible tube portion 13.

In contrast, the second filling agent 52 at the proximal-end-vicinity position of the bending portion 12 is separated frontward from the distal end of the flexible tube portion 13, and is positioned above the distal end side portion 15s and the bending piece 32e being rigid members, where there is a low risk of the occurrence of a crack or the like with the deformation of the flexible tube portion 13. In addition, even if a crack or the like occurs in the second filling agent 52 at the proximal-end-vicinity position of the bending portion 12, the water-tightness is adequately secured because the outer circumference 15sg of the distal end side portion 15s of the connecting member 15 is adhered and fixed on the inner circumference 32en of the bending piece 32e.

Note that, in the present embodiment, as shown in FIG. 2, the outer sheath 23 is fixed on the outer circumference 22g of the braid 22, and the distal end side of the outer sheath 23 is not fixed on the outer circumference 15kg of the proximal end side portion 15k of the connecting member 15, unlike conventional one.

This makes the outer diameter K2 of the above-described connecting portion defined by the outer circumference 52g of the second filling agent 52 smaller than the outer diameter K1 of a conventional connecting portion shown in FIG. 19 (K2 <K1). That is, in the configuration of the present embodiment, the outer diameter is made smaller than the outer diameter of the conventional connecting portion.

Next, the method of connecting the proximal end of the bending portion 12 and the distal end of the flexible tube portion 13 using the connecting member 15 will be described with reference to the above-described FIG. 2, and FIG. 3 to FIG. 5.

Figure 3:
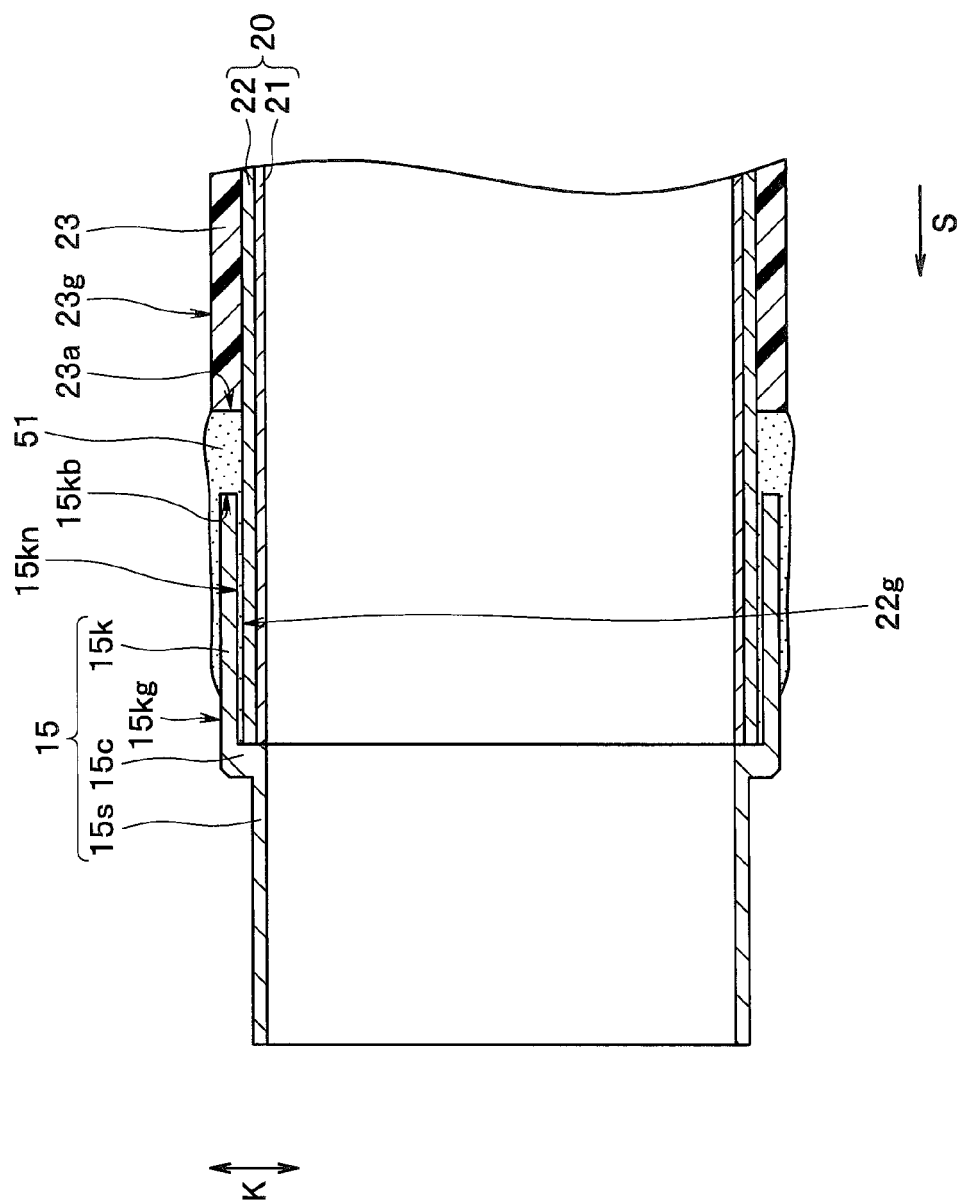
FIG. 3 is a partial cross sectional view showing a state that a flex and a braid are fixed on the inner circumference of a proximal end side portion of a connecting member in FIG. 2 and a first filling agent is applied thereto.
Figure 4:
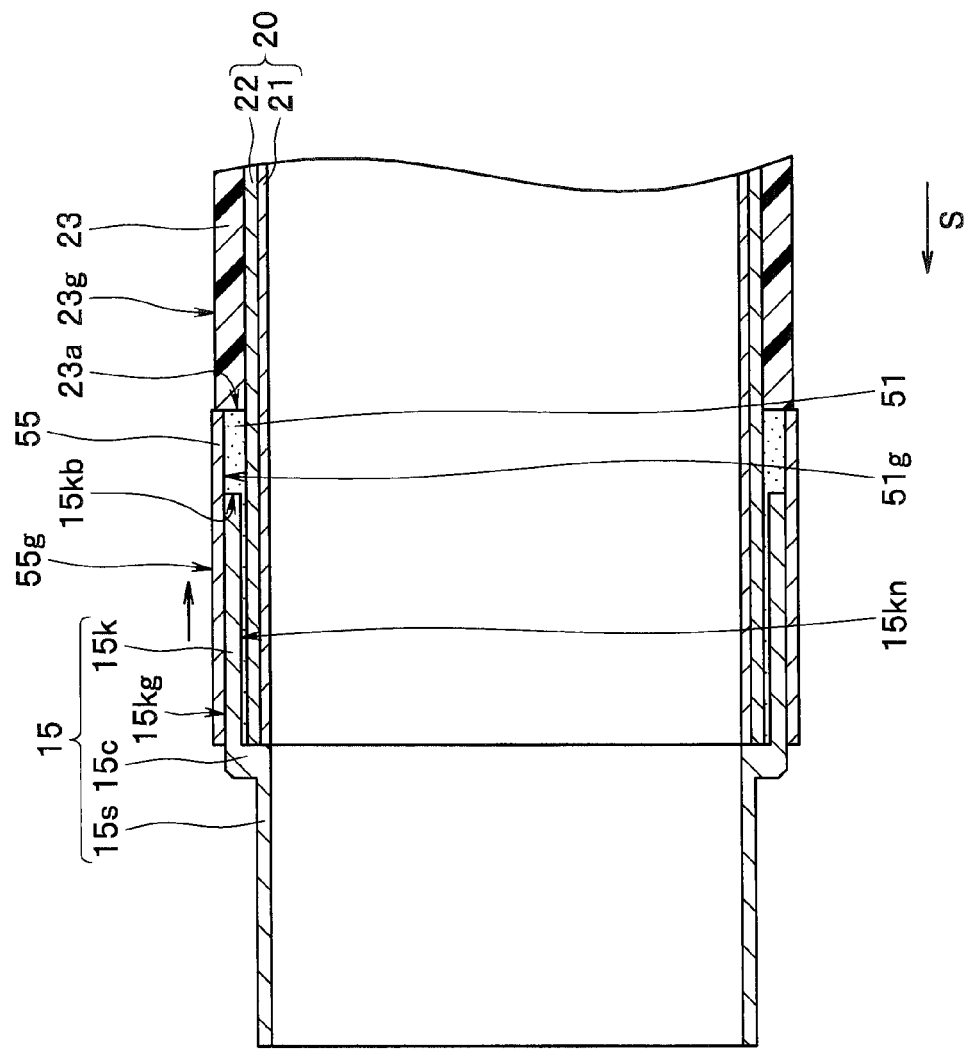
FIG. 4 is a partial cross sectional view showing a state that the outer circumference of the first filling agent in FIG. 3 and the outer circumference of the proximal end side portion of the connecting member are covered with an annular member.
Figure 5:
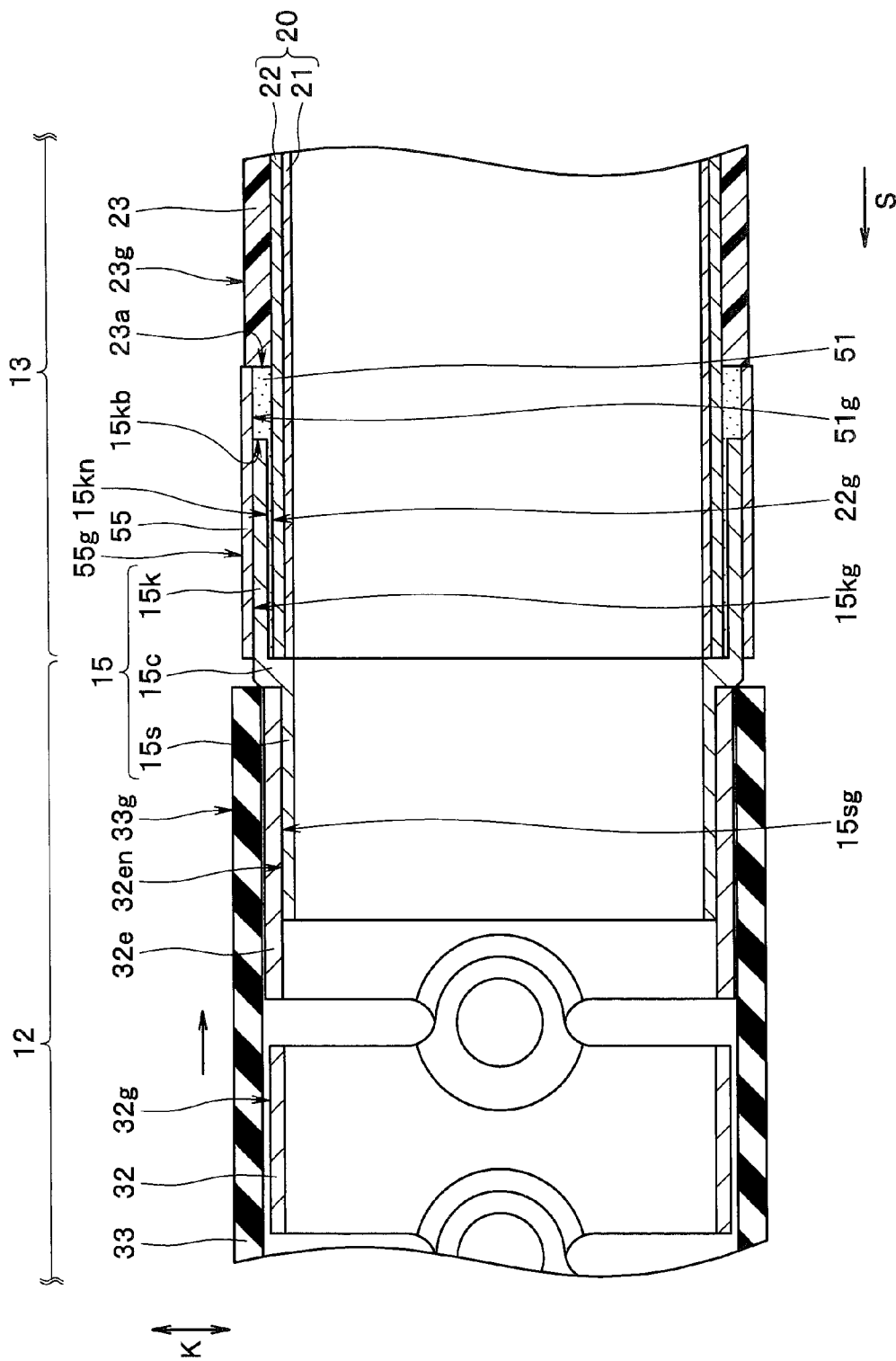
FIG. 5 is a partial cross sectional view showing a state that a bending piece the outer circumference of which is covered with a bending cover is fixed on the outer circumference of a distal end side portion of the connecting member in FIG. 4.

FIG. 3 is a partial cross sectional view showing a state that the flex and the braid are fixed on the inner circumference of the proximal end side portion of the connecting member in FIG. 2 and the first filling agent is applied thereto, FIG. 4 is a partial cross sectional view showing a state that the outer circumference of the first filling agent in FIG. 3 and the outer circumference of the proximal end side portion of the connecting member are covered with the annular member, FIG. 5 is a partial cross sectional view showing a state that the bending piece the outer circumference of which is covered with the bending cover is fixed on the outer circumference of the distal end side portion of the connecting member in FIG. 4.

When connecting the proximal end of the bending portion 12 to the distal end of the flexible tube portion 13, an operator first fixes and adheres the outer circumference 22g on the distal end side of the braid 22 in the flexible member 20 to the inner circumference 15kn of the proximal end side portion 15k of the connecting member 15, as shown in FIG. 3. Subsequently, the distal end 23a of the outer sheath 23 is caused to cover the outer circumference 22g of the braid 22 in such a manner as to be separated rearward from the proximal end 15kb of the proximal end side portion 15k of the connecting member 15. In such a covering state of the outer sheath 23, the first filling agent 51 is applied between the proximal end 15kb of the proximal end side portion 15k and the distal end 23a of the outer sheath 23 on the outer circumference 22g of the braid 22, and to a part of the outer circumference 22g of the braid 22. Note that the connecting member 15, the flexible member 20, and the outer sheath 23 may be assembled in advance, and subsequently connected to the bending portion 12.

Next, the operator moves, as shown in FIG. 4, the annular member 55 from the front in the inserting direction S (hereafter, simply referred to as front) rearward with respect to the outer circumference 15kg of the proximal end side portion 15k of the connecting member 15 and the outer circumference 51g of the first filling agent 51 until the proximal end of the annular member 55 abuts the distal end 23a of the outer sheath 23, so as to cover them. As a result, the annular member 55 is fixed on the outer circumference 15kg of the proximal end side portion 15k of the connecting member 15 and the outer circumference 51g of the first filling agent 51.

Next, the operator inserts, as shown in FIG. 5, the rearmost bending piece 32e on the outer circumference 15sg of the distal end side portion 15s from the front until the bending piece 32e abuts the distal end of the crank portion 15c of the connecting member 15, and adheres and fixes the bending piece 32e. Subsequently, the operator inserts the bending cover 33 on the outer circumferences of the plurality of bending pieces 32 from the front until the proximal end of the bending cover 33 abuts the distal end of the crank portion 15c of the connecting member 15. This makes the bending cover 33 cover the outer circumferences of the bending pieces 32 and to be adhered and fixed.

Last, the operator applies, as shown in FIG. 2, the second filling agent 52 to the outer circumference 33g on the proximal end side of the bending cover 33, the outer circumference 55g of the annular member 55, and the outer circumference 23g of the outer sheath 23, continuously along the inserting direction S. This makes the distal end of the flexible tube portion 13 to be fixed to the proximal end of the bending portion 12 with the connecting member 15.

In such a manner, the present embodiment describes that the distal end 23a of the outer sheath 23 of the flexible tube portion 13 is fixed on the outer circumference 22g of the braid 22 at a position separated rearward from the proximal end 15kb of the proximal end side portion 15k of the connecting member 15. In addition, the present embodiment describes that the first filling agent 51 is applied between the distal end 23a of the outer sheath 23 and the proximal end 15kb of the connecting member 15 on the outer circumference of the braid 22.

In addition, the present embodiment describes that the outer circumference 51g of the first filling agent 51 is covered with the annular member 55, and the second filling agent 52 is applied to the outer circumference 55g of the annular member 55 and the outer circumference 23g on the distal end side of the outer sheath 23 continuously along the inserting direction to covers them.

According to the above, when the insertion portion 2 is inserted into a conduit, the flexible tube portion 13 is twisted, bent, or the like to be deformed, and an external force is provided to the second filling agent 52 at the distal-end-vicinity position of the flexible tube portion 13. As a result, even if a crack or the like occurs at the distal-end-vicinity position of the flexible tube portion 13, the annular member 55 is positioned between the second filling agent 52 and the first filling agent 51 in the radial direction K to separate the second filling agent 52 and the first filling agent 51, which prevents the crack or the like from penetrating the first filling agent 51.

Therefore, even if a crack or the like occurs in the second filling agent 52 the crack or the like does not result in a crack or the like occurring in the first filling agent 51. This enables the water-tightness between the proximal end side portion 15$k$ of the connecting member 15 and the flexible tube portion 13 to be adequately secured with a simple configuration using the first filling agent 51 and the second filling agent 52 without using the binding thread 160, which increases the operability.

In addition, the second filling agent 52 provides the continuous coverage up to the outer circumference 33$g$ on the proximal end side of the bending cover 33 along the inserting direction S, and the outer circumference 15$sg$ of the distal end side portion 15$s$ of the connecting member 15 is adhered and fixed to the bending piece 32$e$. This enables the water-tightness between the distal end side portion 15$s$ of the connecting member 15 and the bending portion 12 to be adequately secured with only the second filling agent 52 without using binding thread 160.

Furthermore, the distal end side of the outer sheath 23 does not cover the outer circumference 15$kg$ of the proximal end side portion 15$k$ of the connecting member 15 unlike conventional configurations, but is configured to cover the outer circumference of the braid 22. Furthermore, the annular member 55 is formed to have a thickness smaller than the thickness of the outer sheath 23 in the radial direction K. This enables the outer diameter K2 in the radial direction of the connecting portion between the proximal end of the bending portion 12 and the distal end of the flexible tube portion 13 to be made smaller than the outer diameter K1 of the conventional connecting portion.

Given the above description, it is possible to provide the endoscope 1 which enables reducing the diameter of and reliably securing the water-tightness of the connecting portion between the bending portion 12 and the flexible tube portion 13, with simplicity and good operability.

Note that a modification of the first embodiment will be described below with reference to FIG. 6. FIG. 6 is a partial cross sectional view showing a state that the outer circumference of the first filling agent in FIG. 2 is positioned, in the radial direction, inside the outer circumference of the proximal end side portion of the connecting member, and the annular member covers only the outer circumference of the first filling agent.

The above-described present embodiment shows, with reference to FIG. 2, that the first filling agent 51 is applied to the outer circumference 22$g$ of the braid 22 such that the outer circumference 51$g$ of the first filling agent 51 has the same outer diameter as the outer circumference 15$kg$ of the proximal end side portion 15$k$ of the connecting member 15.

In addition, the present embodiment shows that the annular member 55 covers the outer circumference 15$kg$ of the proximal end side portion 15$k$ and the outer circumference 51$g$ of the first filling agent 51.

This is not limiting, and as shown in FIG. 6, the first filling agent 51 may be applied in such a manner that the outer circumference 51$g$ is positioned, in the radial direction K, inside the outer circumference 15$kg$ of the proximal end side portion 15$k$ of the connecting member 15. Furthermore, the annular member 55 may be also formed only on the outer circumference 51$g$ of the first filling agent 51 such that the outer circumference 55$g$ of the annular member 55 has the same outer diameter as the outer circumference 15$kg$ of the proximal end side portion 15$k$ of the connecting member 15.

Such a configuration of the modification in FIG. 6 makes the assemblability of the annular member 55 less than the present embodiment. However, the configuration can make the outer diameter of the connecting portion smaller than the present embodiment by the thickness of the annular member 55 in the radial direction K. Note that the other effects are the same as those of the above-described present embodiment.

(Second Embodiment)

Figure 7:
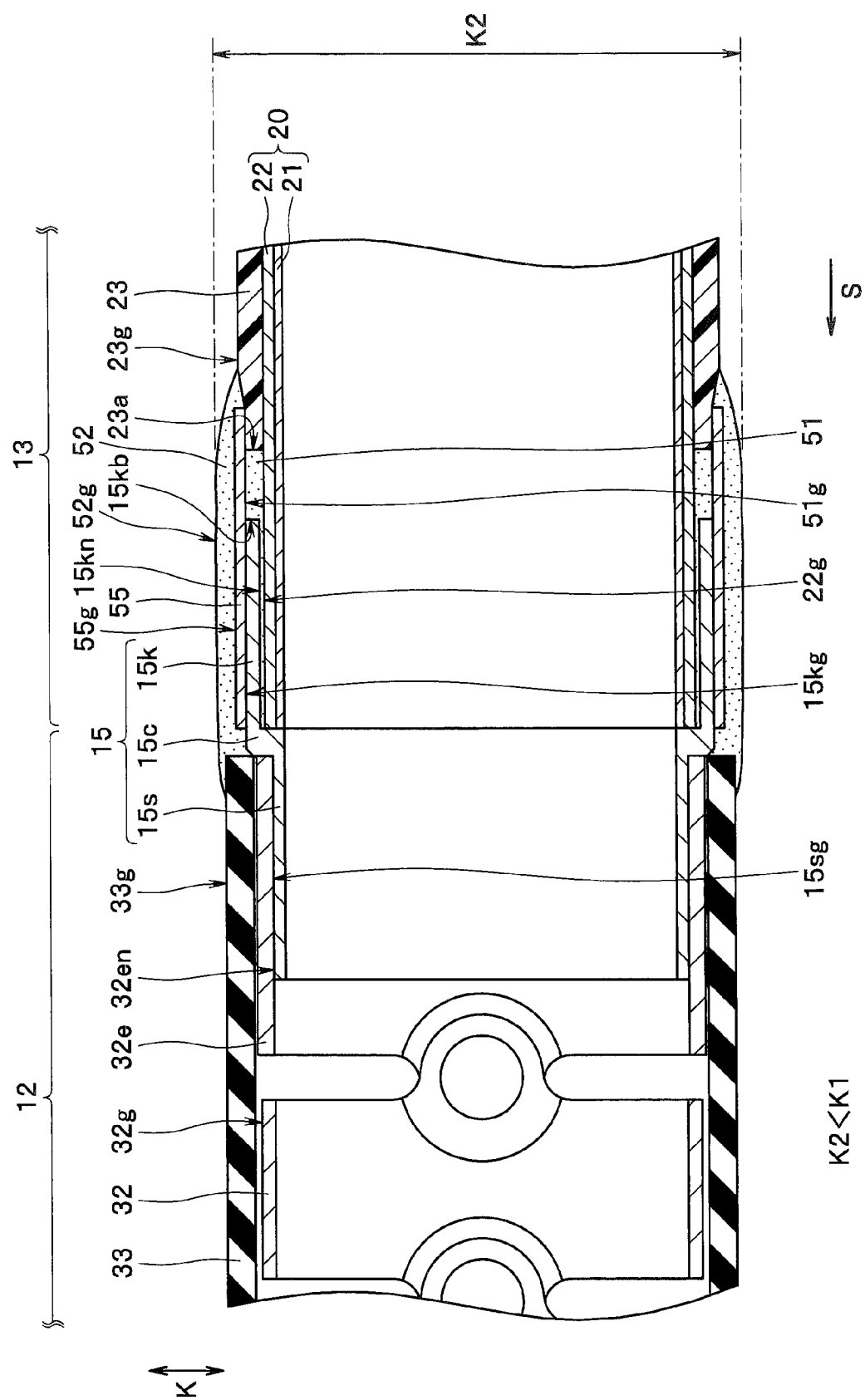
FIG. 7 is a partial cross sectional view showing a connecting portion between the proximal end of the bending portion and the distal end of the flexible tube portion in an insertion portion of an endoscope of a second embodiment of the present invention, under magnification.

FIG. 7 is a partial cross sectional view showing a connecting portion between the proximal end of the bending portion and the distal end of the flexible tube portion in an insertion portion of an endoscope of the present second embodiment, under magnification.

The configuration of the endoscope of this second embodiment is different, as compared with the endoscope of the above-described first embodiment shown in FIG. 1 to FIG. 5, in that the proximal end side of the annular member covers the outer circumference on the distal end side of the outer sheath.

The description will be therefore made only on these points of difference, and components similar to those of the first embodiment will be denoted by the same reference characters, and the description thereof will be omitted.

As shown in FIG. 7, in the present embodiment, the outer circumference 23$g$ on the distal end side of the outer sheath 23 is formed to have the same outer diameter as the outer circumference 15$kg$ of the proximal end side portion 15$k$ and the outer circumference 51$g$ of the first filling agent 51. Furthermore, the proximal end side of the annular member 55 also covers the outer circumference 23$g$ on the distal end side of the outer sheath 23.

Note that, also in the present embodiment, the second filling agent 52 is applied so as to continuously cover the outer circumference 33$g$ on the proximal end side of the bending cover 33, the outer circumference 55$g$ of the annular member 55, and the outer circumference 23$g$ on the distal end side of the outer sheath 23.

In addition, the other configuration is the same as the configuration of the first embodiment. Furthermore, a connecting method in the present embodiment is the same as the above-described first embodiment except that the proximal end side of the annular member 55 is caused to cover the outer circumference 15$kg$ of the proximal end side portion 15$k$ of the connecting member 15 and the outer circumference 23$g$ on the distal end side of the outer sheath 23, and thus the description thereof will be omitted.

In such a configuration, the proximal end side of the annular member 55 covers even the outer circumference 23$g$ on the distal end side of the outer sheath 23, which makes the annular member 55 prevents moisture, cracks or the like from penetrating the first filling agent 51 from the second filling agent 52 more securely than in the first embodiment. Note that the other effects are the same as those of the first embodiment.

(Third Embodiment)

Figure 8:
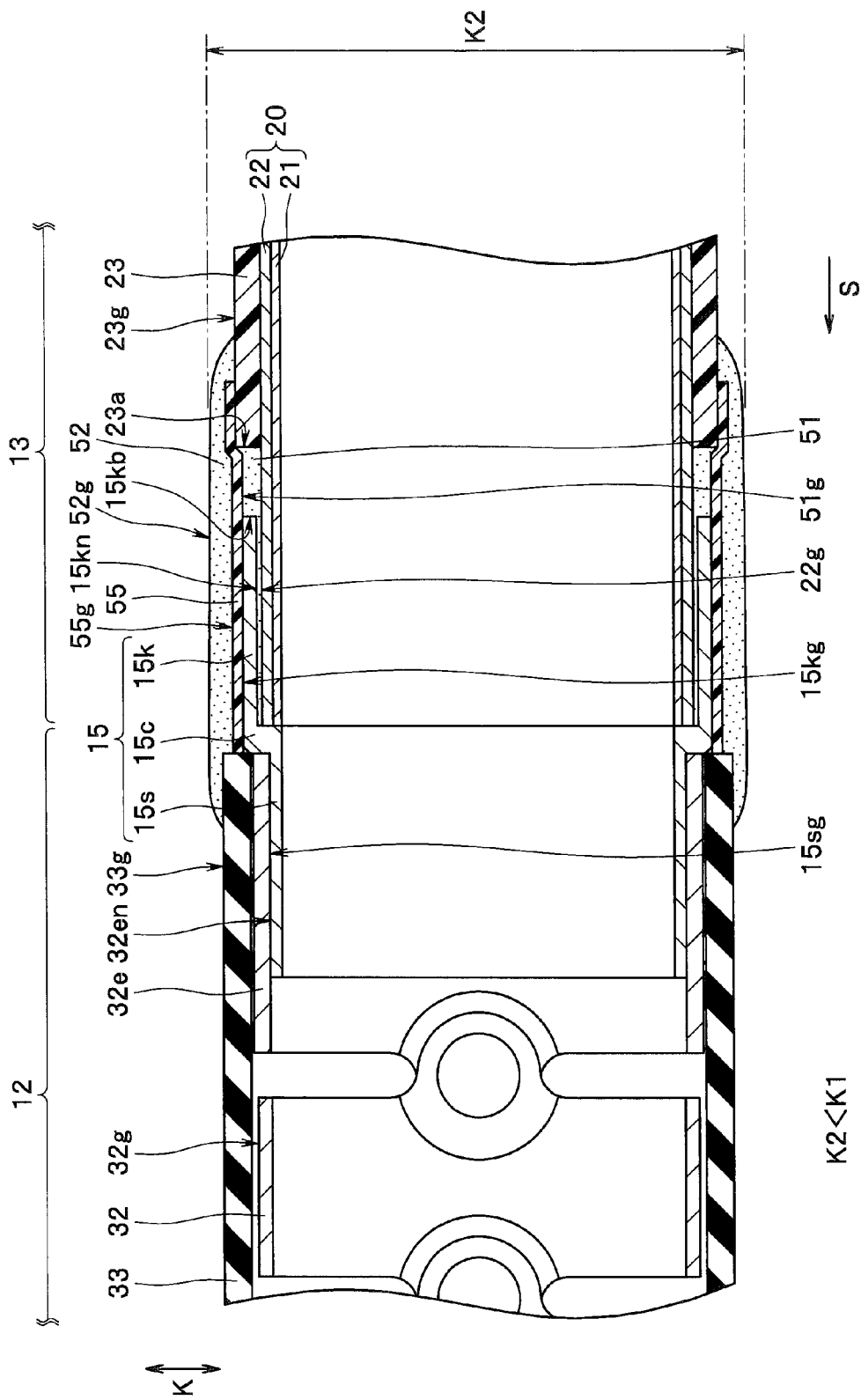
FIG. 8 is a partial cross sectional view showing a connecting portion between the proximal end of the bending portion and the distal end of the flexible tube portion in an insertion portion of an endoscope of a third embodiment of the present invention, under magnification.

FIG. 8 is a partial cross sectional view showing the connecting portion between the proximal end of the bending portion and the distal end of the flexible tube portion in the insertion portion of an endoscope of the present third embodiment, under magnification.

The configuration of the endoscope of this third embodiment is different, as compared with the endoscope of the above-described first embodiment shown in FIG. 1 to FIG. 5, and with the endoscope of the second embodiment shown in FIG. 7, in that the annular member is configured by a heat shrinkable tube.

The description will be therefore made only on these points of difference, and components similar to those of the first and second embodiments will be denoted by the same reference characters, and the description thereof will be omitted.

The above-described first and second embodiments describe that the annular member 55 is configured by a metal or a resin.

This is not limiting, and as shown in FIG. 8, the annular member 55 may be configured by the heat shrinkable tube. In addition, in FIG. 8, the proximal end of the heat shrinkable tube 55 also covers the outer circumference of the distal end side of the outer sheath 23, as with the second embodiment.

Note that, also in the present embodiment, the second filling agent 52 is applied so as to continuously cover the outer circumference 33g on the proximal end side of the bending cover 33, the outer circumference 55g of the heat shrinkable tube 55, and the outer circumference 23g on the distal end side of the outer sheath 23.

In addition, the other configuration is the same as the first and second embodiments. Furthermore, a connecting method in the present embodiment includes covering the outer circumference 15kg of the proximal end side portion 15k of the connecting member 15 and the outer circumference 23g on the distal end side of the outer sheath 23 with the proximal end of the heat shrinkable tube 55 side, and subsequently adding heat to the heat shrinkable tube 55 to shrink. The method except this is the same as the method of the above-described first embodiment, and thus the description thereof will be omitted.

In such a configuration, the annular member 55 configured by the heat shrinkable tube can be formed to have a thickness in the radial direction K smaller than the annular member 55 configured by a metal or a resin. For this reason, it is possible to reduce the outer diameter of the connecting portion, as well as to make the covering operation of the annular member 55 easy. Note that the other effects are the same as those of the first and second embodiments.

(Fourth Embodiment)

Figure 9:
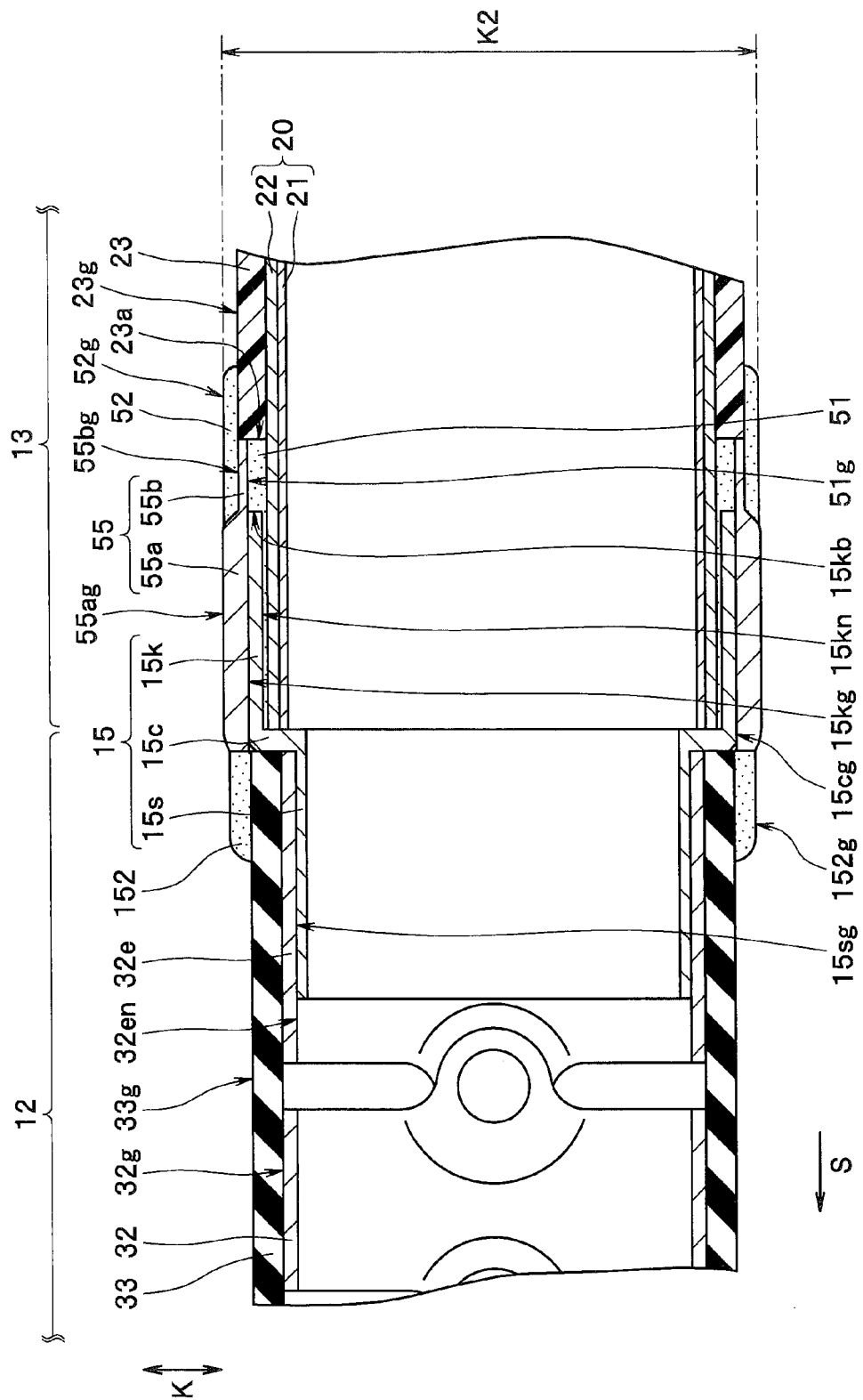
FIG. 9 is a partial cross sectional view showing the connecting portion between the proximal end of the bending portion and the distal end of the flexible tube portion in an insertion portion of an endoscope of a fourth embodiment of the present invention, under magnification.

FIG. 9 is a partial cross sectional view showing the connecting portion between the proximal end of the bending portion and the distal end of the flexible tube portion in the insertion portion of an endoscope of the present fourth embodiment, under magnification.

The configuration of the endoscope of this fourth embodiment is different, as compared with the endoscope of the above-described first embodiment shown in FIG. 1 to FIG. 5, in that the outer circumference of the proximal end side portion of the annular member is formed to have a diameter smaller than the diameter of the outer circumference of the distal end side portion of the annular member, and in that the second filling agent continuously covers the outer circumference of the proximal end side portion of the annular member and the outer circumference on the distal end side of the outer sheath along the inserting direction.

The description will be therefore made only on these points of difference, and components similar to those of the first embodiment will be denoted by the same reference characters, and the description thereof will be omitted.

As shown in FIG. 9, in the present embodiment, the main part of an annular member 55 is configured by a distal end side portion 55a that covers the outer circumference 15kg of the proximal end side portion 15k of the connecting member 15 and the outer circumference 15cg of the crank portion 15c, and a proximal end side portion 55b that covers the outer circumference 51g of the first filling agent 51, and the proximal end of the proximal end side portion 55b abuts the distal end 23a of the outer sheath 23.

Note that the outer circumference 55bg of the proximal end side portion 55b of the annular member 55 is formed to have a diameter smaller than the diameter of the outer circumference 55ag of the distal end side portion 55a, and the outer circumference 55bg is positioned inside the outer circumference 55ag in the radial direction K. More specifically, the outer circumference 55bg is positioned so as to be substantially flush or flush with the outer circumference 23g of the outer sheath 23.

In addition, the second filling agent 52 is applied so as to continuously cover the outer circumference 55bg of the proximal end side portion 55b of the annular member 55 and the distal end side of the outer circumference 23g of the outer sheath 23 along the inserting direction S. This causes the second filling agent 52 to secure water-tightness between the proximal end side portion 55b of the annular member 55 and the distal end 23a of the outer sheath 23.

Note that the second filling agent 52 is applied such that the outer circumference 52g has substantially the same or the same outer diameter as the diameter of the outer circumference 55ag of the distal end side portion 55a of the annular member 55. That is, in the present embodiment, the second filling agent 52 is not applied to the outer circumference of the distal end side portion 55a of the annular member 55 or the outer circumference 33g of the bending cover 33.

In addition, in the present embodiment, the outer circumference 33g on the proximal end side of the bending cover 33 is covered with a filling agent 152 that is adhered to the distal end of the distal end side portion 55a. Note that an outer circumference 152g of the filling agent 152 is positioned, in the radial direction K, inside the outer circumference 55ag of the distal end side portion 55a. This filling agent 152 secures water-tightness between the outer circumference 15sg of the distal end side portion 15s and the inner circumference 32en of the bending piece 32e.

Note that the other configuration is the same as the configuration of the above-described first embodiment. Furthermore, a connecting method in the present embodiment includes covering the outer circumference 15kg of the proximal end side portion 15k of the connecting member 15 and the outer circumference 15cg of the crank portion 15c with the annular member 55, and applying the second filling agent 52 such that the second filling agent 52 continuously covers the outer circumference 55bg of the proximal end side portion 55b of the annular member 55 and the outer circumference 23g on the distal end side of the outer sheath 23 along the inserting direction S. Furthermore, the connecting method includes applying the above-described filling agent 152. The method except this is the same as the method of the first embodiment, and thus the description thereof will be omitted.

As seen from the above, the present embodiment shows that the outer circumference 55bg of the proximal end side portion 55b of the annular member 55 is formed to have a diameter smaller than the outer circumference 55ag of the distal end side portion 55a, and the second filling agent 52 is applied so as to continuously cover the outer circumference 55bg of the proximal end side portion 55b and the distal end side of the outer circumference 23g of the outer sheath 23 along the inserting direction S.

This can make the outer diameter K2 of the connecting portion smaller than the diameter of the first embodiment because the outer circumference 52g of the second filling agent 52 does not protrude outward from the outer circumference 55ag of the distal end side portion 55a of the annular member 55 in the radial direction K.

In addition, the second filling agent 52 is applied in such a manner that the outer circumference 52g has substantially the same or the same outer diameter as the diameter of the outer circumference 55ag of the distal end side portion 55a of the annular member 55, which makes the outer circumference 52g and the outer circumference 55ag flush with each other in the inserting direction S. This makes the second filling agent 52 difficult to be scraped off even when the connecting portion comes into contact with the inner wall or the like of a conduit.

Note that the other effects are the same as those of the above-described first embodiment.

Figure 10:
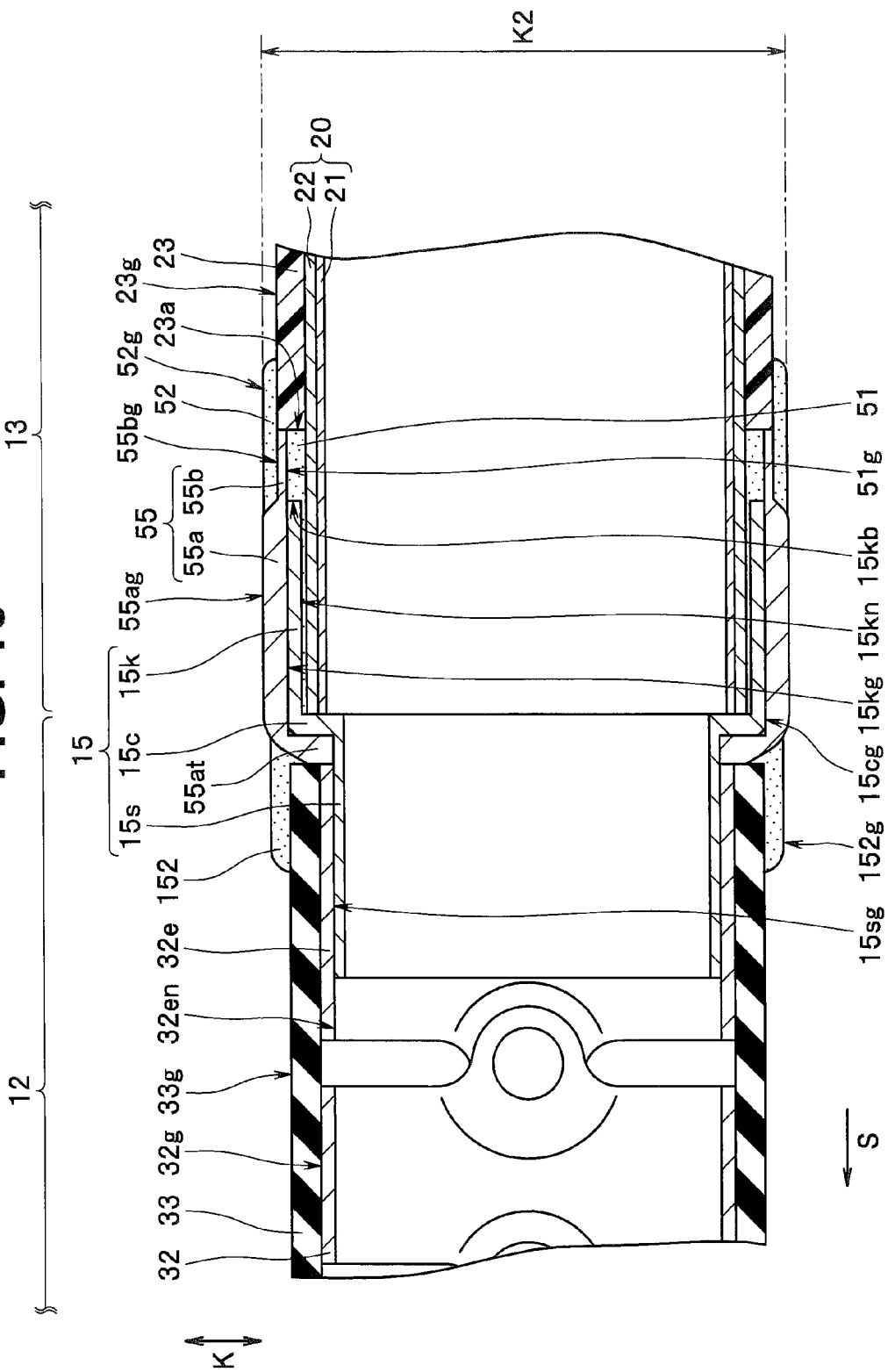
FIG. 10 is a partial cross sectional view showing a modification of a distal end side portion of an annular member in the connecting portion in FIG. 9.

A modification of the present embodiment will be described with reference to FIG. 10. FIG. 10 is a partial cross sectional view showing a modification of the distal end side portion of the annular member in the connecting portion in FIG. 9.

The above-described present embodiment describes, as shown in FIG. 9, that the distal end side portion 55a of the annular member 55 covers the outer circumference 15kg of the proximal end side portion 15k of the connecting member 15 and the outer circumference 15cg of the crank portion 15c in the configuration where the proximal end of the bending cover 33 and the proximal end of the bending piece 32e abut the distal end of the crank portion 15c of the connecting member 15.

This is not limiting, and as shown in FIG. 10, a protruding portion 55at that is bent inward in the radial direction K may be provided to the distal end of the distal end side portion 55a of the annular member 55, bringing about a state that the proximal end of the protruding portion 55at covers the distal end of the crank portion 15c. In this state, the distal end side portion 55a of the annular member 55 may cover the outer circumference 1kg of the proximal end side portion 15k of the connecting member 15 and the outer circumference 15cg of the crank portion 15c. In this case, the proximal end of the bending cover 33 and the proximal end of the bending piece 32e abut the distal end of the protruding portion 55at.

Such a configuration also provides the effects similar to those of the present embodiment, as well as makes the contact area between the filling agent 152 and the distal end side portion 55a of the annular member 55 larger than the configuration of the present embodiment.

(Fifth Embodiment)

Figure 11:
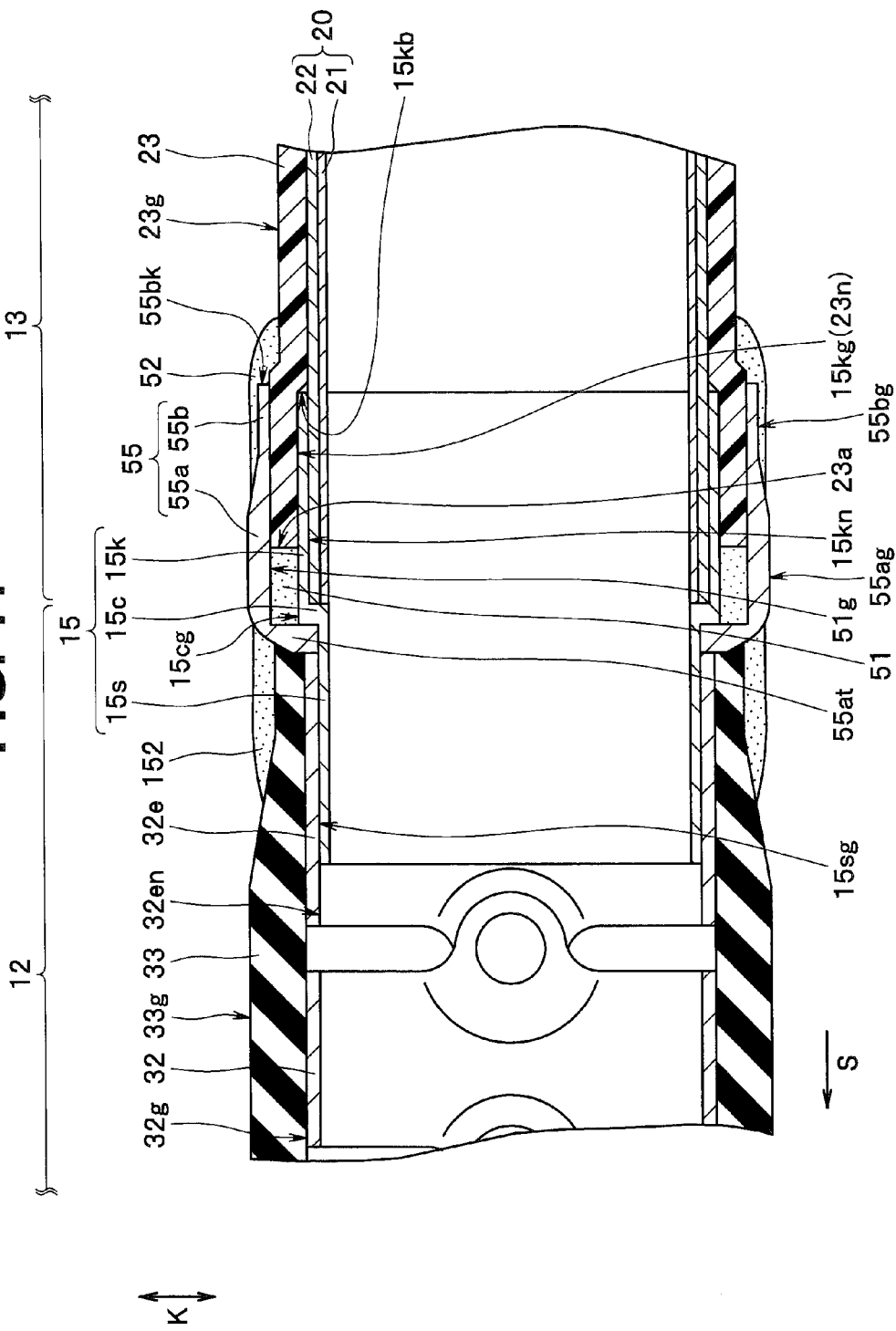
FIG. 11 is a partial cross sectional view showing the connecting portion between the proximal end of the bending portion and the distal end of the flexible tube portion in an insertion portion of an endoscope of a fifth embodiment of the present invention, under magnification.

FIG. 11 is a partial cross sectional view showing the connecting portion between the proximal end of the bending portion and the distal end of the flexible tube portion in an insertion portion of an endoscope of the present fifth embodiment, under magnification.

The configuration of an endoscope of this fifth embodiment is different from, compared with the modification of the endoscope of the fourth embodiment shown in the above-described FIG. 10, in that the inner circumference of the distal end side of the outer sheath is adhered and fixed on the outer circumference of the proximal end side portion of the connecting member, and in that the first filling agent is applied to a region between the distal end of the outer sheath and the protruding portion of the annular member. The description will be therefore made only on these points of difference, and components similar to those in FIG. 10 will be denoted by the same reference characters, and the description thereof will be omitted.

As shown in FIG. 11, in the present embodiment, an inner circumference 23n of the distal end side of the outer sheath 23 is adhered and fixed on the outer circumference 15kg of the proximal end side portion 15k of the connecting member 15.

Note that the distal end 23a of the outer sheath 23 is positioned to be separated rearward from the protruding portion 55at of the annular member 55 at a set interval in the inserting direction S, and the first filling agent 51 is applied to a region between the distal end 23a and the protruding portion 55at on the outer circumference 15cg of the crank portion 15c and the outer circumference 15kg of the proximal end side portion 15k.

Therefore, the main part of the annular member 55 is configured by the distal end side portion 55a that covers the outer circumference 51g of the first filling agent 51 and the outer circumference 23g in the vicinity of the distal end of the outer sheath 23, and the proximal end side portion 55b that covers the outer circumference 23g on the distal end side of the outer sheath 23. Note that the proximal end 55bk of the proximal end side portion 55b is positioned at substantially the same position as the proximal end 15kb of the proximal end side portion 15b in the inserting direction S.

In addition, also in the present embodiment, the outer circumference 55bg of the proximal end side portion 55b of the annular member 55 is formed to have a diameter smaller than the diameter of the outer circumference 55ag of the distal end side portion 55a, and the outer circumference 55bg is positioned inside the outer circumference 55ag in the radial direction K.

In addition, also in the present embodiment, the second filling agent 52 is applied so as to continuously cover the outer circumference 55bg of the proximal end side portion 55b of the annular member 55 and the distal end side of the outer circumference 23g of the outer sheath 23 along the inserting direction S. This causes the second filling agent 52 to secure water-tightness between the proximal end 55bk of the proximal end side portion 55b of the annular member 55 and the distal end 23a of the outer sheath 23.

Note that the other configuration is the same as that of the above-described FIG. 10. In addition, such a configuration also provides the effects similar to those of the above-described FIG. 10.

Figure 12:
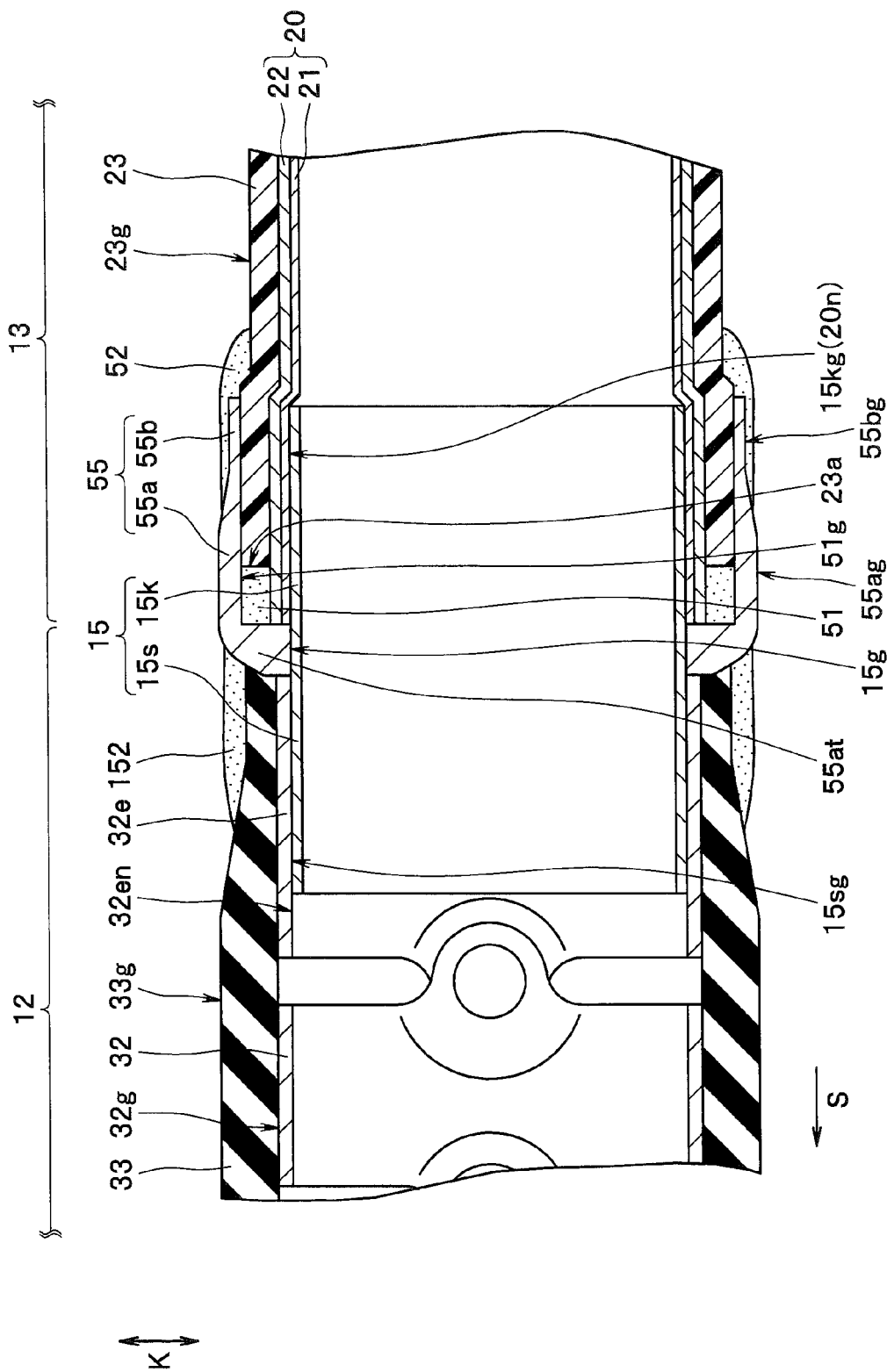
FIG. 12 is a partial cross sectional view showing a modification of the connecting portion between the proximal end of the bending portion and the distal end of the flexible tube portion in the insertion portion of the endoscope in FIG. 11, under magnification.

Now, a modification will be described below with reference to FIG. 12. FIG. 12 is a partial cross sectional view showing a modification of the connecting portion between the proximal end of the bending portion and the distal end of the flexible tube portion in the insertion portion of the endoscope in FIG. 11, under magnification.

In the above-described present embodiment, the connecting member 15 includes the crank portion 15c, as with the above-described first embodiment, and the distal end side portion 15s positioned closer to the distal end side than the crank portion 15c is positioned, in the radial direction K of the insertion portion 2, inside the proximal end side portion 15k positioned closer to the proximal end side than the crank portion 15c.

This is not limiting, and as shown in FIG. 12, the connecting member 15 may be elongated along the inserting direction S, and may be configured by a tubular member having a uniform outer diameter along the inserting direction S, including a distal end side portion 15s to be a front end portion in the inserting direction S and a proximal end side portion 15k to be a rear portion.

Also in such a configuration, as with the above-described present embodiment, the inner circumference 32*en* of the bending piece 32*e* is adhered and fixed on the outer circumference 15*sg* of the distal end side portion 15*s* of the connecting member 15. In addition, the protruding portion 55*at* of the annular member 55 abuts the outer circumference 15*g* at a position between the distal end side portion 15*s* and the proximal end side portion 15*k* in the inserting direction S.

In addition, the above-described present embodiment describes that the inner circumference 23*n* of the distal end side of the outer sheath 23 is adhered and fixed on the outer circumference 15*kg* of the proximal end side portion 15*k* of the connecting member 15.

This is not limiting, and as shown in FIG. 12, the inner circumference 20*n* on the distal end side of the flexible member 20 may be adhered and fixed on the outer circumference 15*kg* of the proximal end side portion 15*k* of the connecting member 15, in a state that the distal end of the flexible member 20 is caused to abut the protruding portion 55*at*.

In addition, the outer sheath 23 may be adhered and fixed on the outer circumference of the distal end side of the flexible member 20, that is, the outer circumference on the distal end side of the braid 22, in such a manner that the distal end 23*a* of the outer sheath 23 is positioned to be separated rearward from the protruding portion 55*at* at the set interval in the inserting direction S. That is, the outer circumference 15*kg* of the proximal end side portion 15*k* of the connecting member 15 is covered with the distal end side of the outer sheath 23 together with the distal end side of the flexible member 20.

Furthermore, the first filling agent 51 is applied to a region between the distal end 23*a* and the protruding portion 55*at* on the outer circumference of the flexible member 20 in the inserting direction S.

Note that the other configuration is the same as that of the above-described present embodiment. Such a configuration also provides the similar effects to those of the present embodiment.

Figure 13:
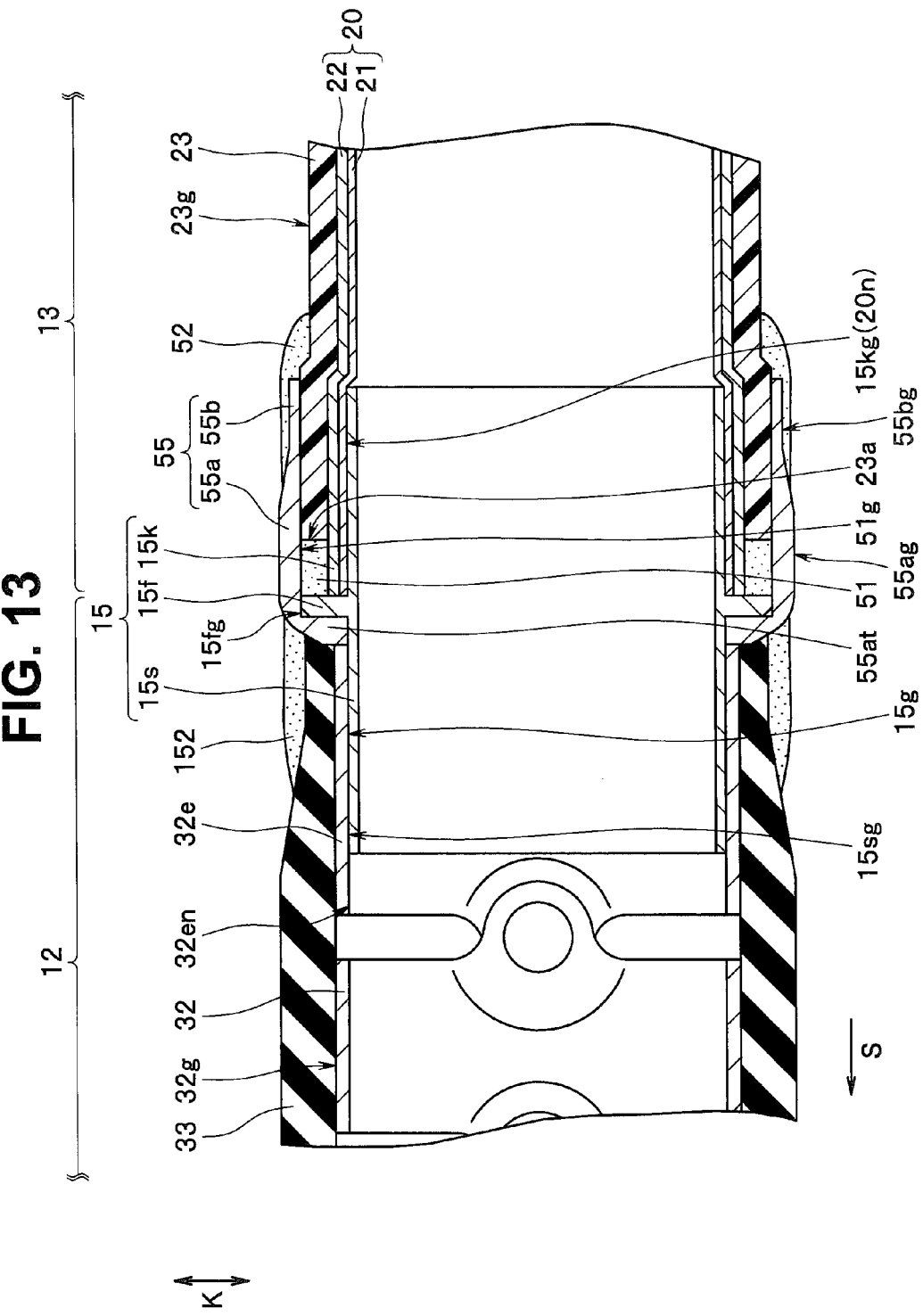
FIG. 13 is a partial cross sectional view showing a modification, other than FIG. 12, of the connecting portion between the proximal end of the bending portion and the distal end of the flexible tube portion in the insertion portion of the endoscope in FIG. 11, under magnification.

In addition, another modification will be described below with reference to FIG. 13. FIG. 13 is a partial cross sectional view showing a modification, other than FIG. 12, of the connecting portion between the proximal end of the bending portion and the distal end of the flexible tube portion in the insertion portion of the endoscope in FIG. 11, under magnification.

The connecting portion between the proximal end of the bending portion 12 and the distal end of the flexible tube portion 13 shown in FIG. 13 is different in configuration from the connecting portion in FIG. 12 in that the connecting member 15 includes an outward flange 15*f* formed being extended outward in the radial direction K on the outer circumference 15*g* at the halfway position in the inserting direction S.

In the connecting portion in FIG. 13, the inner circumference 20*n* on the distal end side of the flexible member 20 is adhered and fixed on the outer circumference 15*kg* of the proximal end side portion 15*k* of the connecting member 15, in a state that the distal end of the flexible member 20 is caused to abut the outward flange 15*f*.

In addition, in the connecting portion in FIG. 13, the distal end 23*a* of the outer sheath 23 covered with the outer circumference of the flexible member 20 is positioned to be separated rearward from the outward flange 15*f* at the set interval in the inserting direction S.

Furthermore, in the connecting portion in FIG. 13, the first filling agent 51 is applied to a region between the outward flange 15*f* and the distal end 23*a* of the outer sheath 23 in the inserting direction S on the outer circumference of the distal end side of the flexible member 20.

In addition, in the connecting portion in FIG. 13, the distal end side portion 55*a* of the annular member 55 covers the outer circumference 15*fg* of the flange 15*f*, the outer circumference 51*g* of the first filling agent 5, and the outer circumference 23*g* in the vicinity of the distal end of the outer sheath 23. In addition, the protruding portion 55*at* is caused to abut the outer circumference 15*sg* of the distal end side portion 15*s* on the distal end side of the flange 15*f* in the inserting direction S.

Note that the other configuration is the same as the configuration in FIG. 12. Such a configuration of the connecting portion shown in FIG. 13 can also provide the effects similar to those of the configuration of the connecting portion in FIG. 12.

Figure 14:
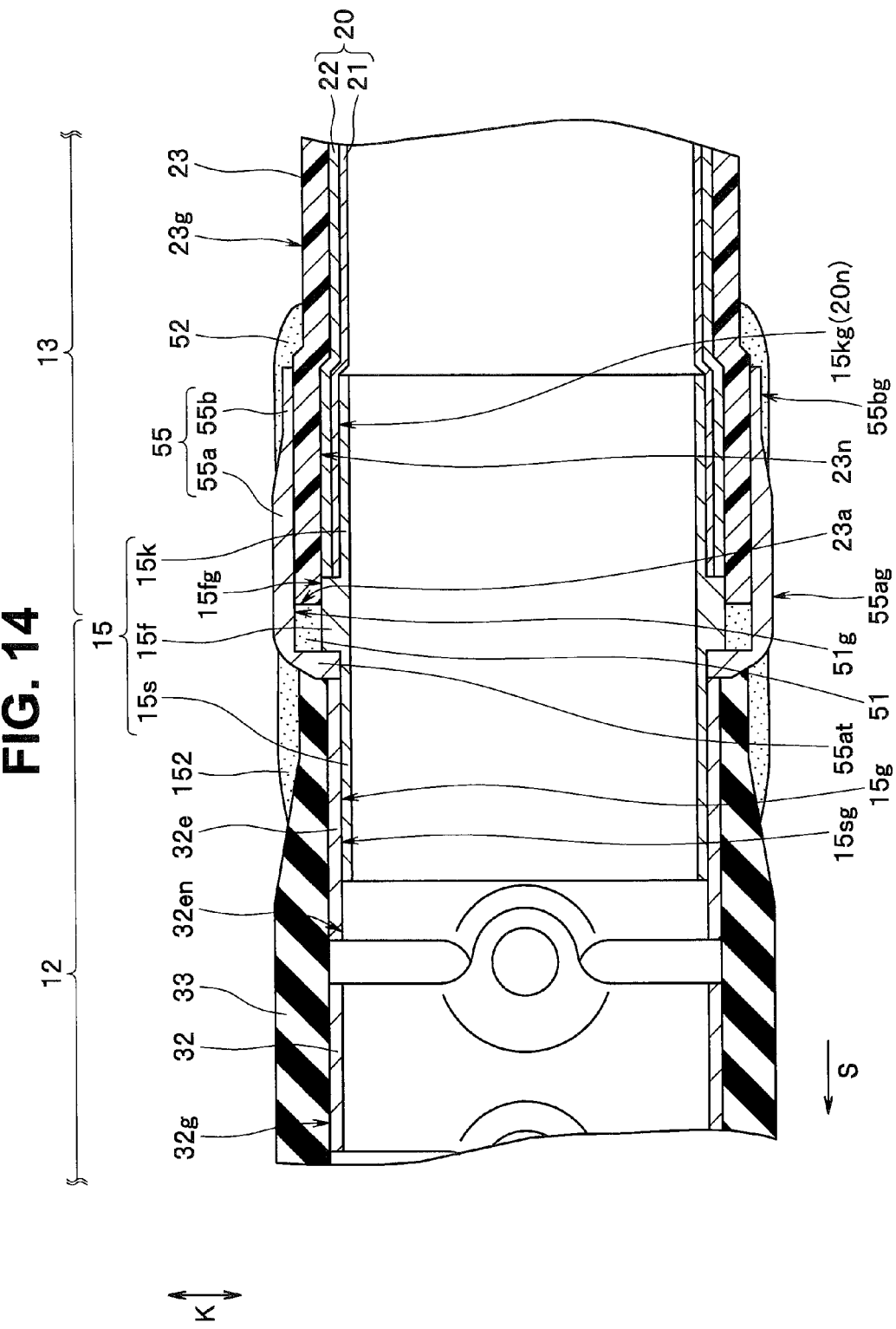
FIG. 14 is a partial cross sectional view showing a modification, other than FIG. 13, of the connecting portion between the proximal end of the bending portion and the distal end of the flexible tube portion in the insertion portion of the endoscope in FIG. 11, under magnification.

In addition, yet another modification will be described below with reference to FIG. 14. FIG. 14 is a partial cross sectional view showing a modification, other than FIG. 13, of the connecting portion between the proximal end of the bending portion and the distal end of the flexible tube portion in the insertion portion of the endoscope in FIG. 11, under magnification.

The connecting portion between the proximal end of the bending portion 12 and the distal end of the flexible tube portion 13 shown in FIG. 14 is different in configuration from the connecting portion in FIG. 13 in that the outward protruding-portion length of the outward flange 15*f* in the radial direction K is shorter than that in FIG. 13, and in that the extension length of the outward flange 15*f* in the inserting direction S is longer than that in FIG. 13.

The connecting portion in FIG. 14, as with the connecting portion in FIG. 13, the inner circumference 20*n* on the distal end side of the flexible member 20 is adhered and fixed on the outer circumference 15*kg* of the proximal end side portion 15*k* of the connecting member 15 in a state that the distal end of the flexible member 20 is caused to abut the outward flange 15*f*.

In addition, the outer circumference of the distal end side of the flexible member 20 is covered with the inner circumference 23*n* of the distal end side of the outer sheath 23, and the inner circumference 23*n* also covers a part of the outer circumference 15*fg* of the outward flange 15*f*. As a result, in the inserting direction S, the distal end 23*a* of the outer sheath 23 is positioned to be separated rearward from the protruding portion 55*at* at a set interval.

In addition, in the connecting portion in FIG. 14, the first filling agent 51 is applied to a region between the protruding portion 55*at* of the annular member 55 and the distal end 23*a* of the outer sheath 23 in the inserting direction S on the outer circumference 15*fg* of the outward flange 15*f*.

Furthermore, in the connecting portion in FIG. 14, the distal end side portion 55*a* of the annular member 55 covers the outer circumference 51*g* of the first filling agent 51 and the outer circumference 23*g* on the distal end side of the outer sheath 23.

Note that the other configuration is the same as the configuration in FIG. 13. Such a configuration of the connecting portion shown in FIG. 14 can also provide the effects similar to those of the configuration of the connecting portion in FIG. 13.

(Sixth Embodiment)

Figure 15:
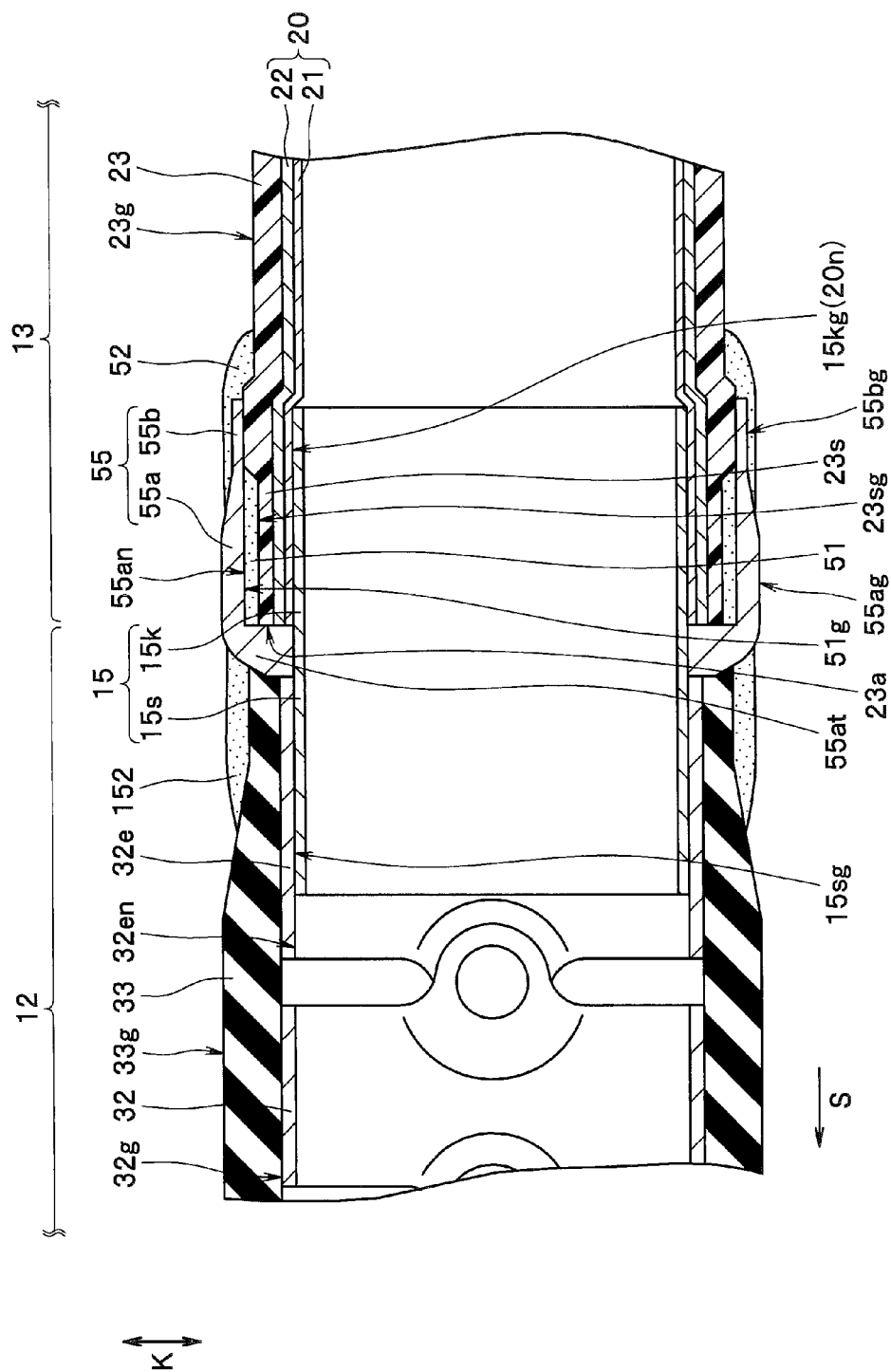
FIG. 15 is a partial cross sectional view showing the connecting portion between the proximal end of the bending portion and the distal end of the flexible tube portion in an insertion portion of an endoscope of a sixth embodiment of the present invention, under magnification.

FIG. 15 is a partial cross sectional view showing the connecting portion between the proximal end of the bending portion and the distal end of the flexible tube portion in an insertion portion of an endoscope in the present sixth embodiment, under magnification.

An endoscope of this sixth embodiment is different in configuration from the modification of the endoscope of the fifth embodiment shown in the above-described FIG. 12, in that the distal end of the outer sheath is caused to abut the protruding portion of the annular member, in that the distal end side of the outer sheath is formed to have a thickness smaller than the other portion, and in that the first filling agent is applied between the outer circumference of the thin-walled portion of the distal end side of the outer sheath and the inner circumference of the distal end side portion of the annular member. The description will be therefore made only on these points of difference, and components similar to those in FIG. 12 will be denoted by the same reference characters, and the description thereof will be omitted.

As shown in FIG. 15, in the present embodiment, the distal end 23a of the outer sheath 23 is caused to abut the protruding portion 55at of the annular member 55.

In addition, the distal end side of the outer sheath 23 is formed to have a thickness in the radial direction K smaller than the other portion of the outer sheath 23. That is, a thin-walled portion 23s is formed to the distal end side of the outer sheath 23. Note that this makes an outer circumference 23sg of the thin-walled portion 23s separated from an inner circumference 55an of the distal end side portion 55a of the annular member 55 at a set interval in the radial direction K.

Furthermore, the first filling agent 51 is applied to a region in the radial direction K between the outer circumference 23sg and the inner circumference 55an of the distal end side portion 55a of the annular member 55, on the outer circumference 23sg of the thin-walled portion 23s.

Therefore, the distal end side portion 55a of the annular member 55 covers the outer circumference 51g of the first filling agent 51, and the proximal end side portion 55b covers a portion on the distal end side of the outer sheath 23 closer to the proximal end side than the thin-walled portion 23s.

Note that the other configuration is the same as the configuration in the above-described FIG. 12. Such a configuration can also provide the effects similar to those of the above-described FIG. 12.

In addition, the above-described first to sixth embodiments have described, by way of example, the configuration where the flexible member 20 has the flex 21, but this is not limiting, and a tubular member configured by a resin may be used instead of the flex 21.

Furthermore, the flexible member 20 may have a configuration where the inner circumference and the outer circumference of the braid 22 is covered with the tubular member configured by a resin, that is, a configuration where the braid 22 is sandwiched in the radial direction K by two tubular members configured by a resin.

Figure 16:
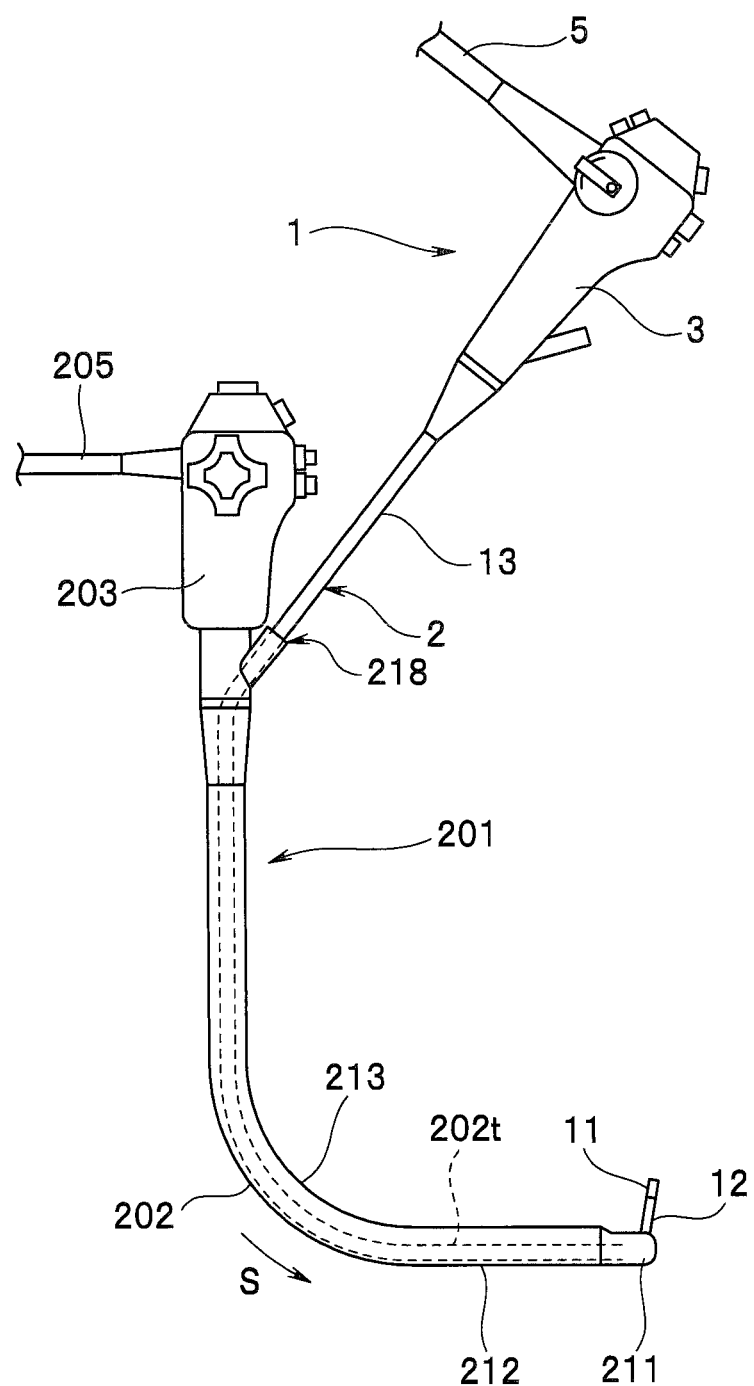
FIG. 16 is a diagram showing the configuration of an endoscope system where the insertion portion of the endoscope in FIG. 1 can be inserted into a channel of an insertion portion of another endoscope.

FIG. 16 is a diagram showing the configuration of an endoscope system where the insertion portion of the endoscope in FIG. 1 can be inserted into a channel of the other insertion portion of the endoscope.

As shown in FIG. 16, the insertion portion 2 of the endoscope 1 shown in the above-described first to third embodiments may be insertable to a channel 202t provided in an insertion portion 202 of another endoscope 201.

More specifically, as shown in FIG. 16, the endoscope 201 includes the insertion portion 202 that includes a distal end portion 211, a bending portion 212, and a flexible tube portion 213, and an operating portion 203 that is provided being connected to the proximal end of the insertion portion 202. In addition, the endoscope 201 includes a universal cord 205 that is extended from the operating portion 203, and although not shown, a connector that is provided to the extension end of the universal cord 205 and is detachable from an external device.

The insertion portion 202 includes a channel 202t formed therein. The distal end of the channel 202t has an opening in a side face of the distal end portion 211, and the proximal end of the channel 202t has an opening toward a treatment instrument insertion opening 218 that is provided to the operating portion 203.

The insertion portion 2 of the endoscope 1 is insertable into the channel 202t via the treatment instrument insertion opening 218, and after insertion, the distal end portion 11 and the bending portion 12 of the insertion portion 2 is caused to protrude laterally with respect to the inserting direction S from the opening in the side face of the distal end portion 211.

Note that for such an endoscope system including the endoscope 1 and the endoscope 201, examples of the endoscope 201 include a side-view type endoscope used to observe laterally with respect to the inserting direction S. In addition, examples of the endoscope 1 include a cholangioscope that is inserted into a bile duct via the channel 202t.

Figure 17:
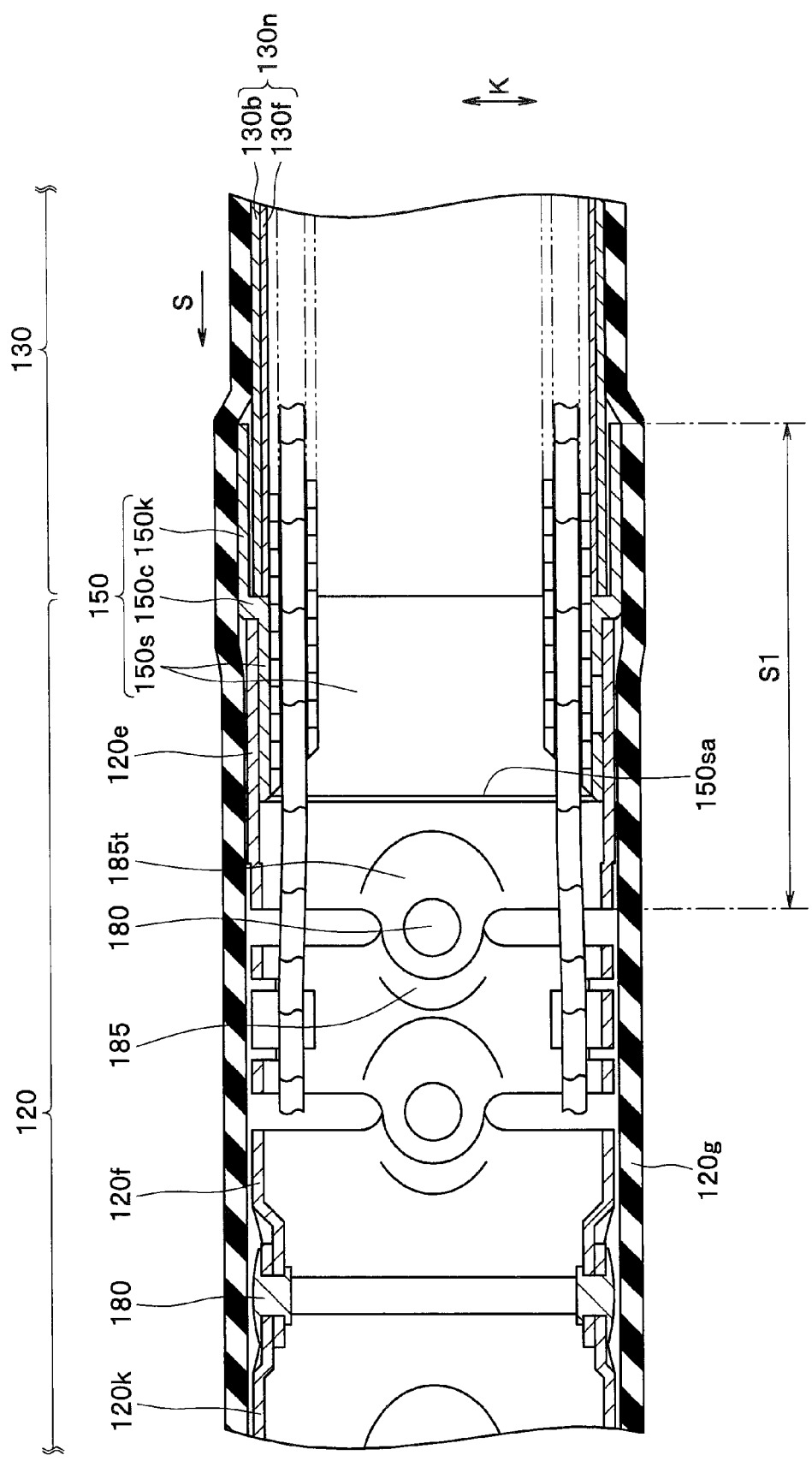
FIG. 17 is a partial cross sectional view showing a connection configuration between the proximal end of the bending portion and the distal end of the flexible tube portion different from FIG. 19 (conventional example)
Figure 18:
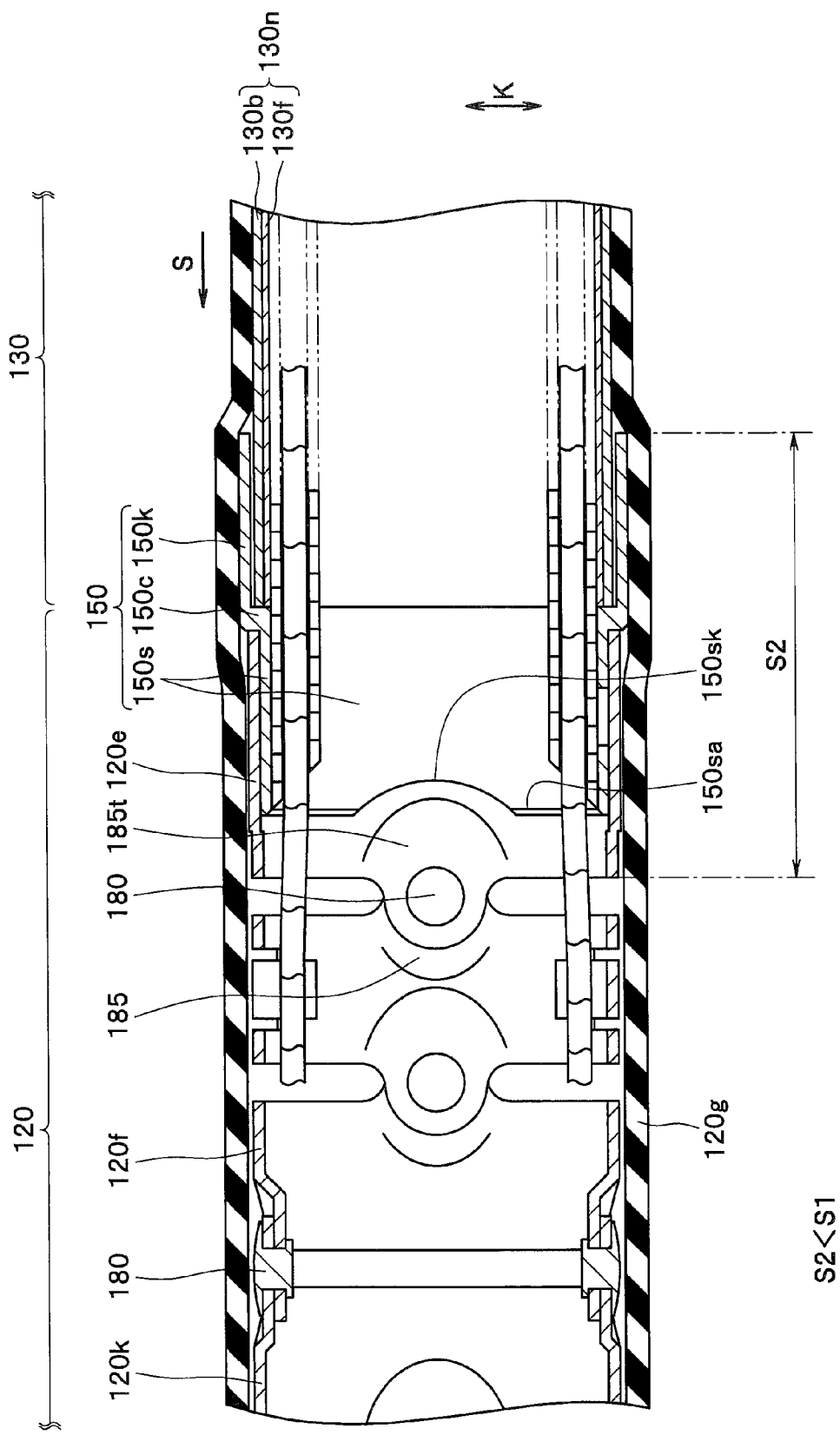
FIG. 18 is a partial cross sectional view showing a connection configuration between the proximal end of the bending portion and the distal end of the flexible tube portion of this configuration.

FIG. 17 is a partial cross sectional view showing the connection configuration between the proximal end of the bending portion and the distal end of the flexible tube portion different from FIG. 19 (conventional example), and FIG. 18 is a partial cross sectional view showing the connection configuration between the proximal end of the bending portion and the distal end of the flexible tube portion of the present configuration.

Note that the description will be therefore made only on these points of difference, and in FIG. 17 and FIG. 18, components similar to those in FIG. 19 will be denoted by the same reference characters, and the description thereof will be omitted. In addition, in FIG. 17 and FIG. 18, unlike FIG. 19, a bending cover 120g is formed to have such a length that the outer circumference of a braid 130b is covered. That is, the proximal end of the bending cover 120g is positioned on the outer circumference of the braid 130b, and covers the outer circumference of the braid 130b.

Now, as shown in FIG. 17, in the conventional connection configuration between the proximal end of the bending portion 120 and the distal end of the flexible tube portion 130, a bending piece 120e, which is positioned at the most rearward position out of a plurality of bending pieces 120k and is fixed on the outer circumference of the distal end side portion 150s of the connecting member 150, is bendably connected to a bending piece 120f that is the forward piece next to the bending piece 120e in the inserting direction S, with a rivet 180.

In addition, at a portion of the bending piece 120e through which the rivet 180 is caused to pass, a lug portion 185 is typically provided having a projecting portion 185t that is engageable with a recessed portion of the bending piece 120f and projects in a depth direction on the surface of the sheet of FIG. 17.

However, the formation of the projecting portion 185t forces a distal end 150sa of the distal end side portion 150s to be positioned at a position rearward a little from the projecting portion 185t in the bending piece 120e as a structure fixed on the outer circumference of the distal end side portion 150s, in order to avoid abutting the projecting portion 185t.

For this reason, it is inevitable to set the length of a rigid portion in the inserting direction S in the connecting portion between the proximal end of the bending portion 120 and the distal end of the flexible tube portion 130 (hereafter, referred to as a rigid-portion length) S1 at a longer length in the inserting direction S.

This results in the reduction of the insertability and the operability of the insertion portion, and in addition, as shown in FIG. 16, when the insertion portion is inserted into the channel 202t of the other insertion portion 202, the connecting portion of the endoscope 1 may be caught on a treatment instrument raising stand for the endoscope 201 that is provided to the channel 202t in the distal end portion 211 of the insertion portion 202, and the endoscope 1 may be thereby damaged.

However, securing the strength of the connecting portion requires the rigid-portion length of the connecting portion to some extent in the configuration where the connection is made using the connecting member 150. That is, it is required to keep the fitting-portion length of the bending piece 120e to some extent with respect to the outer circumference of the distal end side portion 150s, which raises a problem in that the rigid-portion length cannot be made shorten than the rigid-portion length S1.

Thus, in the present configuration, as shown in FIG. 18, an arc-shaped notch 150sk is provided for keeping the projecting portion 185t away, at the position of the distal end 150sa that abuts the projecting portion 185t of the distal end side portion 150s, bringing about a state that the projecting portion 185t is kept away by the notch 150sk. In this state, the bending piece 120e is fixed on the outer circumference of the distal end side portion 150s.

Such a configuration enables the distal end of the distal end side portion 150s to be shifted forward by the rearward depth of the notch 150sk while securing the fitting-portion length of the bending piece 120e with respect to the outer circumference of the distal end side portion 150s as long as the length in FIG. 17. This allows a rigid-portion length S2 of the connecting portion to be shorter than the rigid-portion length S1 in FIG. 17 (S2<S1) while securing the strength of the connecting portion.

The insertability and the operability of the insertion portion are therefore increased, and in addition, the connecting portion of the endoscope 1 is prevented from being caught on the treatment instrument raising stand of the endoscope 201 when being inserted into the channel 202t of the insertion portion 202 of the other endoscope, which can prevent the damage of the endoscope 1.

The present invention is not limited to the above-described embodiments, and various alterations, modifications and the like are possible without departing from the spirit of the present invention.

What is claimed is:

1. An endoscope comprising:
    an elongated insertion portion that is inserted into a subject, the insertion portion comprising:
        a first cylindrical member that extends along an inserting direction of the insertion portion;
        a connecting member having a proximal end side being fixed to a distal end side of the first cylindrical member;
        a first covering member that covers, in a radial direction, an outer circumference of the first cylindrical member, at least a distal end side of the first covering member being positioned outside of an outer circumference of the connecting member in the radial direction, the first covering member being positioned on the proximal end side of the connecting member;
        a first filling agent applied on an outer circumference side of the first cylindrical member in the radial direction such that the first filling agent contacts with at least the distal end side of the first covering member;
        an annular member that covers, in the radial direction, at least an outer circumference of the first filling agent;
        a protruding portion formed on a distal end side of the annular member, the protruding portion extending inward in the radial direction such that the protruding portion abuts an outer circumference of the connecting member, the protruding portion being positioned distally with respect to the distal end of the first covering member; and
        a second filling agent applied to cover, in the radial direction, at least a portion of the outer circumference of the annular member and an outer circumference on the distal end side of the first covering member.

2. The endoscope according to claim 1, wherein
    an outer circumference on the distal end side of the first cylindrical member is fixed on an inner circumference on the proximal end side of the connecting member, and an inner circumference on the distal end side of the first covering member is fixed on the outer circumference on the proximal end side of the connecting member, and
    a region to which the first filling agent is applied is formed between the distal end of the first covering member and the protruding portion.

3. The endoscope according to claim 1, wherein
    an inner circumference on the distal end side of the first cylindrical member is fixed on the outer circumference on the proximal end side of the connecting member, and a distal end of the first cylindrical member abuts the protruding portion of the annular member, and
    a region to which the first filling agent is applied is formed between the distal end of the first covering member and the protruding portion.

4. The endoscope according to claim 1, wherein
    an inner circumference on the distal end side of the first cylindrical member is fixed on an outer circumference on the proximal end side of the connecting member, and a distal end of the first cylindrical member and the distal end of the first covering member abuts the protruding portion of the annular member,
    the distal end side of the first covering member is formed to have a thickness in the radial direction smaller than other portions of the first covering member, and
    a region to which the first filling agent is applied is formed between an outer circumference of a thin-walled portion on the distal end side of the first covering member and an inner circumference of the annular member.

5. The endoscope according to claim 1, wherein the annular member further covers the outer circumference on the distal end side of the first covering member.

6. The endoscope according to claim 5, wherein the annular member is a heat shrinkable tube.

7. The endoscope according to claim 1, wherein a proximal end side portion of the annular member is formed to have a thickness in the radial direction smaller than a diameter of the first covering member, or is formed to have an outer circumference diameter which is smaller than an outer circumference of a distal end side portion of the annular member.

8. The endoscope according to claim 1, wherein the first filling agent has a hardness lower than a hardness of the second filling agent.

9. The endoscope according to claim 1, wherein the first cylindrical member includes a flexible member and the first covering member is an outer sheath that covers an outer circumference of the flexible member in the radial direction.

10. The endoscope according to claim 1, wherein the annular member is formed in such a manner that a diameter of an outer circumference of a proximal end side portion in the inserting direction is smaller than a diameter of an outer circumference of a distal end side portion in the inserting direction.

11. The endoscope according to claim 1, wherein the insertion portion further comprising a second cylindrical member positioned distally to the first cylindrical member, an outer circumference of the second cylindrical member being covered with a second covering member, wherein
the connecting member connects the first cylindrical member and the second cylindrical member along the inserting direction in such a manner that an outer circumference on a distal end side in the inserting direction is fixed on an inner circumference on a proximal end side of the second cylindrical member.

12. The endoscope according to claim 11, wherein the second filling agent is applied so as to cover, in the radial direction, an outer circumference on a proximal end side of the second covering member and the outer circumference of the annular member.

13. The endoscope according to claim 1, wherein the insertion portion is insertable into a channel that is provided in an insertion portion of an other endoscope.

14. An endoscope comprising:
an elongated insertion portion that is to be inserted into a subject, the insertion portion comprising:
a first cylindrical member that extends along an inserting direction of the insertion portion;
a connecting member having a proximal end side being fixed to a distal end side of the first cylindrical member, the connecting member including an outward flange formed on an outer circumference of the connecting member, a distal end of the first cylindrical member abutting the outward flange;
a first covering member that covers, in a radial direction, an outer circumference of the first cylindrical member;
a first filling agent applied on an outer circumference side of the first cylindrical member in the radial direction such that the first filling agent contacts with at least a distal end side of the first covering member;
an annular member that covers, in the radial direction, at least an outer circumference of the first filling agent; and
a second filling agent applied to cover, in the radial direction, at least a portion of the outer circumference of the annular member and an outer circumference on the distal end side of the first covering member.

15. The endoscope according to claim 14, wherein
an inner circumference on the distal end side of the first cylindrical member is fixed on the outer circumference of the connecting member at a position proximal to the outward flange, and
a region to which the first filling agent is applied is formed between a distal end of the first covering member and the outward flange.

16. The endoscope according to claim 14, wherein
at least the distal end side of the first covering member is positioned, in the radial direction, outside the outer circumference on the proximal end side of the connecting member, and a protruding portion is formed on a distal end side of the annular member, the protruding portion extending inward in the radial direction such that the protruding portion abuts an outer circumference of the connecting member,
an inner circumference on the distal end side of the first cylindrical member is fixed on the outer circumference of the connecting member at a position proximal to the outward flange, the protruding portion of the annular member abuts the outer circumference of the connecting member at a position distal to the flange, and an inner circumference on the distal end side of the first covering member is fixed to a part of an outer circumference of the outward flange, and
a region to which the first filling agent is applied is formed between the distal end of the first covering member and the protruding portion.

* * * * *